United States Patent [19]

Freidinger et al.

[11] Patent Number: 5,185,331
[45] Date of Patent: Feb. 9, 1993

[54] TRIAZOLOBENZODIAZEPINES

[75] Inventors: Roger M. Freidinger, Lansdale; Mark G. Bock, Hatfield; Ben E. Evans, Lansdale, all of Pa.

[73] Assignee: Merck & Co., Inc., Rahway, N.J.

[21] Appl. No.: 699,850

[22] Filed: May 14, 1991

[51] Int. Cl.[5] .......................................... A61K 31/55
[52] U.S. Cl. ..................................................... 514/220
[58] Field of Search ........................................ 514/220

[56] References Cited

U.S. PATENT DOCUMENTS

| 4,663,321 | 5/1987 | Bock et al. | 514/220 |
| 4,820,834 | 4/1989 | Evan et al. | 514/220 |
| 07/852,478 | 3/1992 | Freidinger et al. | 514/220 |

FOREIGN PATENT DOCUMENTS

| 411668 | 2/1991 | European Pat. Off. |
| 90/11773 | 4/1989 | World Int. Prop. O. |

OTHER PUBLICATIONS

Bradwejn, et al., *Enhanced Sensitivity to Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291, (1988).
Bradwejn, et al., *Benzodiazepines Antagonize Cholecystokinin-Induced Activation of Rat*, Hippocampal, Nature 312, p. 22, (1984).
de Montigny, *Cholecystokinin Tetrapeptide Induces Panic-like Attacks in Healthy Volunteers*, Arch. Gen. Psychiatry, 46, (1989).
Dourish, et al., *Morphine Induced Analgesia in the Rat Paw Pressure Test is Blocked by CCK and Enhanced by the CCK Antagonist MK-329*, Eur. Jour. Pharm. 147, No. 3, pp. 469–472, (1988).
Bouthillier, et al., *Long-term Benzodiazepine Treatment Reduces Neuronal Responsiveness to Cholecystokinin: an Electrophysiological Study in the Rat*, Eur. Jour. Pharm. 151, No. 1, pp. 135–138, (1988).

*Primary Examiner*—S. J. Friedman
*Attorney, Agent, or Firm*—Mark R. Daniel; Joseph F. DiPrima

[57] ABSTRACT

Pharmaceutical compositions containing Triazolobenzodiazepines of the formula:

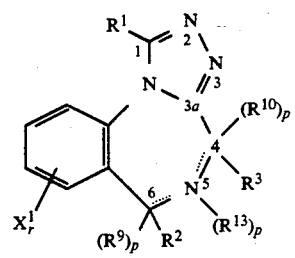

are disclosed which are useful in the treatment of panic disorder or anxiety disorder.

6 Claims, No Drawings

TRIAZOLOBENZODIAZEPINES

BACKGROUND OF THE INVENTION

This application is related to Merck U.S. Pat. No. 4,663,321. Cholecystokinin (CCK) is a neuropeptide composed of thirty-three aminoacids in its originally isolated form. See: Mutt and Jorpes, *Biochem. J.* 125 678 (1971). Also occurring in circulation are 39, 12 and 8 amino acid forms. The carboxyl terminal octapeptide (CCK-8) is the minimum active sequence. Gastrin occurs in 34, 17, and 14 amino acid forms in circulation and is related to CCK by identity of the C-terminal pentapeptides Gly-Trp-Met-Asp-Phe-NH$_2$. Gastrin and CCK exist in both gastrointestinal tissue and the central nervous system. V. Mutt, *Gastrointestinal Hormones*, G. B. J. Glass, Ed., Raven Press, N.Y., p. 169 and G. Nisson, ibid, p. 127.

The isolation of the 33-amino acid polypeptide, cholecystokinin (CCK-33), from porcine intestine, Mutt, V. et al., "Structure of Porcine Cholecystokininpancreozymin. 1. Cleavage with Thrombin and Trypsin", *European J. Biochem.* 6, 156, (1968), was followed by the discovery that it occurs in numerous molecular forms at various sites throughout the peripheral and central nervous systems, Larsson, L. et al., "Localization and Molecular Heterogeneity of Cholecystokinin in the Central and Peripheral Nervous System", *Brain Res.*, 165, 201 (1979). In the mammalian brain the predominant fragments are the carboxy terminal octapeptide, H-Asp-Tyr(SO$_3$H)-Met-Gly-Trp-Met-Asp-Phe-NH$_2$ (CCK-8s, CCK$_{26-33}$) and tetrapeptide, CCK-4 (CCK$_{30-33}$).

The carboxy terminal octapeptide possesses the full biological profile of CCK, Dockray, G. J. et al., "Isolation, Structure and Biological Activity of Two Cholecystokinin Octapeptides from Sheep Brain", *Nature* 274, 711 (1978), and meets many anatomical and biochemical criteria which characterize a neurotransmitter, Vanderhaeghen, J. J. et al., "J. Neuronal Cholecystokinin", *Ann. N.Y. Acad. Sci.*, 448, (1985). The presence of high concentrations of CCK-8s in the mammalian CNS is complemented with findings of specific and high affinity membrane-bound CCK binding sites, Innis, R. B. et al., "Distinct Cholecystokinin Receptors in Brain and Pancreas", *Proc. Natl. Acad. Sci. U.S.A.*, 77, 6917 (1980).

Evidence that more than one form of CCK receptor might exist was first provided in 1980 by Innis and Snyder, Innis, R. B. et al., "Distinct Cholecystokinin Receptors in Brain and Pancreas", *Proc. Natl. Acad. Sci. U.S.A.*, 77, 6917 (1980). At present, CCK receptors have been differentiated into primarily two subtypes based on their affinity for CCK fragments and analogues, Innis, R. B. et al., "Distinct Cholecystokinin Receptors in Brain and Pancreas", *Proc. Natl. Acad. Sci. U.S.A.*, 77, 6917 (1980). The subsequent development of agents which discriminate between different CCK receptor types afforded further support for these assignments, Chang, R. S. L. et al., "Biochemical and Pharmacological Characterization of an Extremely Potent and Selective Nonpeptide Cholecystokinin Antagonist", *Proc. Natl. Acad. Sci. U.S.A.*, 83, 4923 (1986).

The CCK-A receptors, previously known as peripheral CCK receptors, are located in organs such as the pancreas, gallbladder, and colon. They exhibit high affinity for CCK-8s and a lower affinity for the corresponding desulphated fragment, CCK-8d, for CCK-4, and gastrin. Recent autoradiographic results have localized CCK-A receptors in the brain as well, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

The majority of the CCK receptors in the brain are of the CCK-B type. These were previously designated as central CCK receptors. CCK-B receptors are widely distributed throughout the brain and display high affinity for CCK-8s, CCK-4, and pentagastrin, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

In addition to the above mentioned CCK receptor subtypes is a third type, the stomach gastrin receptor, which appears to be closely related to the CCK-B receptor subtype, Beinfeld, M. C., "Cholecystokinin in the Central Nervous System; a Minireview", *Neuropeptides*, 3, 4111 (1983). The minimum fully potent CCK sequence at this receptor is CCK-4, Gregory, R. A., "A Review of some Recent Development in the Chemistry of the Gastrins", *Biorg. Chem.*, 8,497 (1979).

A wide range of physiological responses has been attributed to CCK. In an effort to elucidate its biological roles, researchers have relied primarily on a collection of CCK-A antagonists which has been steadily supplemented and improved to now include very selective, high-affinity agents, Evans, B. E., "Recent Developments in Cholecystokinin Antagonist Research," *Drugs Future*, 14, 971 (1989). In addition to their value as investigative tools, CCK antagonists retain considerable therapeutic potential, Gertz, B. J., "Potential Clinical Applications, of a CCK Antagonist in Cholecystokinin Antagonists," Alan R. Liss, Inc.: New York, pp. 327 (1988).

In recent years, interest in agonists and antagonists of CCK has been stimulated by the possible clinical application of such compounds, Silverman, M. A. et al., "Cholecystokinin Receptor Antagonists, a Review", *Am. J. Gastroenterol*, 82, 703, (1987). The discovery of the presence of CCK in the brain and its significance in relation to its modulation of dopaminergic functions, effects on satiety, its roles in nociception, in anxiety, and other brain functions, Vanderhaeghen, J. J., et al., "J. Neuronal Cholecystokinin", *Ann. N.Y. Acad. Sci.* 448 (1985) has understandably intensified the search for CCK-B selective agents. Since the relevant biologically active fragment, CCK-8s, has a half-life of less than 1 hour, Deschodt-Lanckman, K., et al., "Degradation of Cholecystokinin-like Peptides by a Crude Rat Brain Synaptosomal Fraction: a Study by High Pressure Liquid Chromatography", *Reg. Pept.*, 2, 15 (1981), implicit in the development of candidates for clinical use are criteria of high potency, selectivity, long in-vivo duration, oral bioavailability, and capability of penetrating the blood-brain barrier. These are strict prerequisites, given the tenuous stature of peptides as drugs, Veber, D. F., et al., "The Design of Metabolically-stable Peptide Analogs", *Trends Neurosci.* 8, 392 (1985).

Nevertheless, by employing stratagems which stabilize peptide structures, advances have been made toward developing highly potent and selective peptidal CCK-B receptor ligands Charpentier, B. et al., "Cyclic Chloleycstokinin Analogues with High Selectivity for Central Receptors". *Proc. Natl. Acad. Sci. U.S.A.*, 85, 1968, (1988). Analogues are now available which have proven resistant to enzymatic degradation Charpentier, B. et al., "Enzyme-resistant CCK Analogs with High Affinities for Central Receptors", *Peptides*, 9 835 (1988). Despite favorable receptor binding profiles, this class of compounds fails to meet previously cited key requirements which characterize a drug candidate. In response, researchers have turned to non-peptide compounds which offer a broader range of structure and physicochemical properties.

SUMMARY OF THE INVENTION

It has now been found that pharmaceutical compositions containing the compounds of Formula I are useful in the treatment of panic disorder or anxiety disorder in a mammal, especially a human. The compounds of Formula I are also useful in the treatment of oncologic disorders, controlling pupil constriction in the eye, treating pain or inducing analgesia, or treating a withdrawal response produced by chronic treatment or abuse of drugs or alcohol.

DETAILED DESCRIPTION OF THE INVENTION

The pharmaceutical compositions of this invention contain compounds of Formula I:

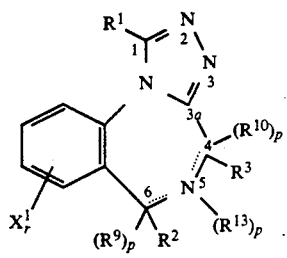

wherein $R^1$ is H, OH, loweralkyl, cycloloweralkyl, loweralkenyl, substituted or unsubstituted phenyl (wherein the substituents may be 1 or 2 of halo, loweralkyl, loweralkoxy, or hydroxy), —(CH$_2$)$_m$NR$^4$R$^5$, CX$^{10}$$_3$, or —(CH$_2$)$_n$COOR$^6$;

$R^2$ is H, loweralkyl, substituted or unsubstituted phenyl (wherein the substitutents may be 1 or 2 of halo, loweralkyl, loweralkoxy, loweralkylthio, carboxyl, carboxyloweralkyl, nitro, —CF$_3$,

or hydroxy), or —(CH$_2$)$_m$COOR$^6$;

$R^3$ is

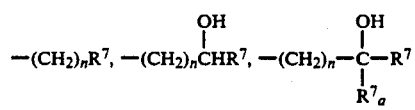

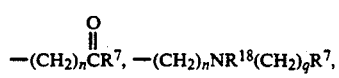

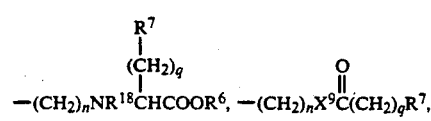

-continued

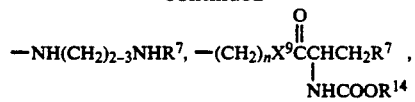

—NH(CH$_2$)$_{2-3}$NHCOR$^7$,

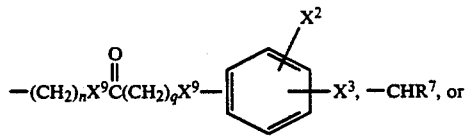

—(CH$_2$)$_n$NR$^{18}$SO$_2$(CH$_2$)$_q$R$^7$,

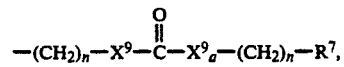

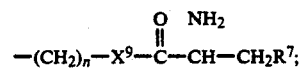

$R^4$ and $R^5$ are independently H, loweralkyl, or cycloloweralkyl or are connected to form a hetero ring

wherein n is 2–6;

$R^6$ is H, loweralkyl, cycloloweralkyl, substituted or unsubstituted phenyl (wherein the substituents may be 1 or 2 of halo, loweralkyl, loweralkoxy, nitro, or CF$_3$), or substituted or unsubstituted phenylloweralkyl (wherein the substituents may be 1 or 2 of halo, loweralkyl, loweralkoxy, nitro, or CF$_3$);

$R^7$ and $R^7{}_a$ are independently α- or β-naphthyl, substituted or unsubstituted phenyl (wherein the substituents may be 1 to 2 of halo, —NO$_2$, —OH, —NR$^4$R$^5$, loweralkyl, cyano, phenyl, trifluoromethyl, acetylamino, acetyloxy, loweralkylthio, SCF$_3$, C≡CH, CH$_2$SCF$_3$, OCHF$_2$, SH, S-phenyl, PO$_3$H, or loweralkoxy),

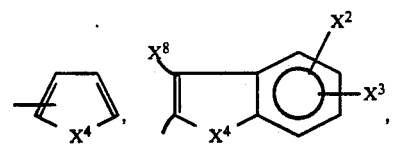

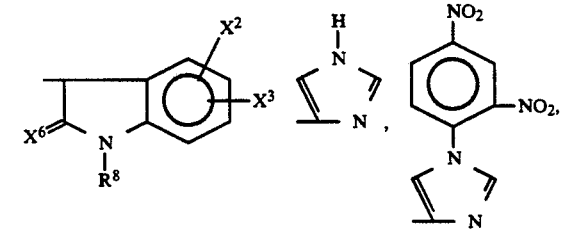

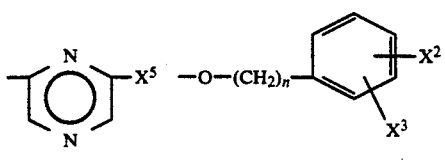

-continued

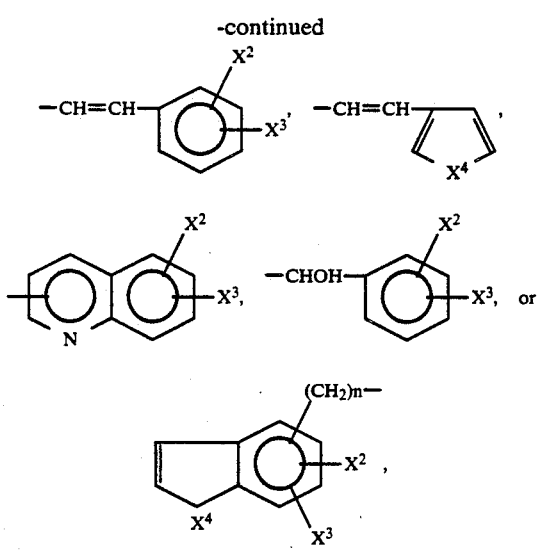

(with the proviso that q is not 0 or 1 in -(CH$_2$)$_n$NH(CH$_2$)$_q$R$^7$ and that q is not 0 in

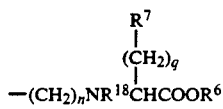

when R$^7$ or R$^7_a$ is

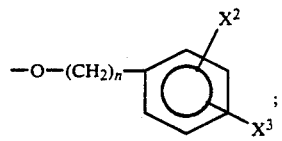

R$^8$ is H, loweralkyl, cycloloweralkyl, —(CH$_2$)$_m$CONH$_2$, —(CH$_2$)$_m$COOR$^6$, -(CH$_2$)$_n$-cycloloweralkyl, —(CH$_2$)$_m$NR$^4$R$^5$,

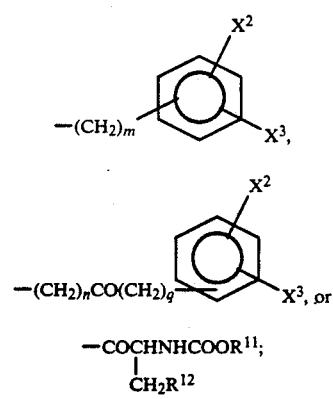

—COCHNHCOOR$^{11}$;
  |
  CH$_2$R$^{12}$

R$^9$ and R$^{10}$ are independently H, -OH, or -CH$_3$;
R$^{11}$ and R$^{12}$ are independently loweralkyl or cycloloweralkyl;
R$^{13}$ is H, loweralkyl, acyl, O, or cycloloweralkyl;
R$^{14}$ is loweralkyl or phenylloweralkyl;
R$^{18}$ is H, loweralkyl, or acyl;
m is 1–4;
n is 0–4;

p is 0 when its adjacent===is unsaturated and 1 when its adjacent===is saturated, except that when R$^{13}$ is O, p=1 and===is unsaturated;
q is 0–4;
r is 1 or 2;
X$^1$ is H, —NO$_2$, CF$_3$ CN, OH, loweralkyl, halo, loweralkylthio, loweralkoxy, —(CH$_2$)$_n$COOR$^6$, —NR$^4$R$^5$, or

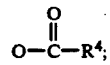

X$^2$ and X$^3$ are independently H, -OH, -NO$_2$, halo, loweralkylthio, loweralkyl, loweralkoxy or

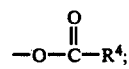

X$^4$ is S, O, CH$_2$, or NR$^8$;
X$^5$ is H, CF$_3$, CN, -COOR$^6$, NO$_2$, or halo;
X$^6$ is O or HH;
X$^8$ is H or loweralkyl;
X$^9$ and X$^9_a$ are independently NR$^{18}$, O;
X$^{10}$ is F, Cl, Br;
  is a saturated or unsaturated bond; or a pharmaceutically acceptable salt thereof, and a pharmaceutically acceptable carrier.

As used herein, the definition of each expression, e.g. m, n, p, loweralkyl, etc., when it occurs more than once in any structure, is intended to be independent of its definition elsewhere in the same structure. Thus, the ring fragment

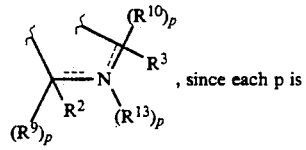, since each p is independently 1 or 0, represents the three structures

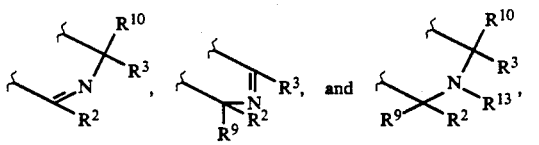

when R$^{13}$ is not O.

As used herein, halo is F, Cl, Br, or I; loweralkyl is 1–4 carbon straight or branched chain alkyl and includes methyl, ethyl, propyl, isopropyl, butyl, isobutyl, and t-butyl; in loweralkoxy and loweralkylthio, the alkyl portion is loweralkyl as previously defined; cycloloweralkyl is cycloalkyl of 3–5 carbons; loweralkenyl is 1–5 carbon straight or branched chain alkenyl; and acyl is formyl, acetyl, propionyl, or butyryl. Loweralkyl is also 1–5 carbon straight or branched chain alkyl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, p-aminobenzoic, p-acetamidobenzoic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

The pharmaceutically acceptable salts of the acid of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

The compounds of Formula I may further be useful in the treatment or prevention of additional central nervous system disorders including neurological and pyschiatric disorders. Examples of such central nervous system disorders include anxiety disorder and panic disorder. Additional examples of central nervous system disorders include panic syndrome, anticipatory anxiety, phobic anxiety, panic anxiety, chronic anxiety, and endogenous anxiety.

The compounds of Formula I may further be useful in the treatment of oncologic disorders. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit moisis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to cocaine, alcohol or nicotine.

The compounds of Formula I or pharmaceutically acceptable salts thereof, can be administered to a human subject either alone, or preferably, in combination with pharmaceutically acceptable carriers or diluents, in a pharmaceutical composition, according to standard pharmaceutical practice. The compounds can be administered orally or parenterally. Parenteral administration includes intravenous, intramuscular, intraperitoneal, subcutaneous and topical administration.

For oral use of an antagonist of CCK or gastrin of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight administered in single or divided doses.

In some cases, however, it may be necessary to use dosage levels outside these limits. For example, doses as low as about 1 ng/kg, about 0.005 μg to about 0.05 μg, or about 100 ng to about 100 μg/kg may be administered.

In the effective treatment of panic syndrome, panic disorder, anxiety disorder and the like, preferably about 0.05 mg/kg to about 0.5 mg/kg of CCK antagonist maybe administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

The compounds of Formula I are prepared according to the following schemes.

REACTION SCHEME I
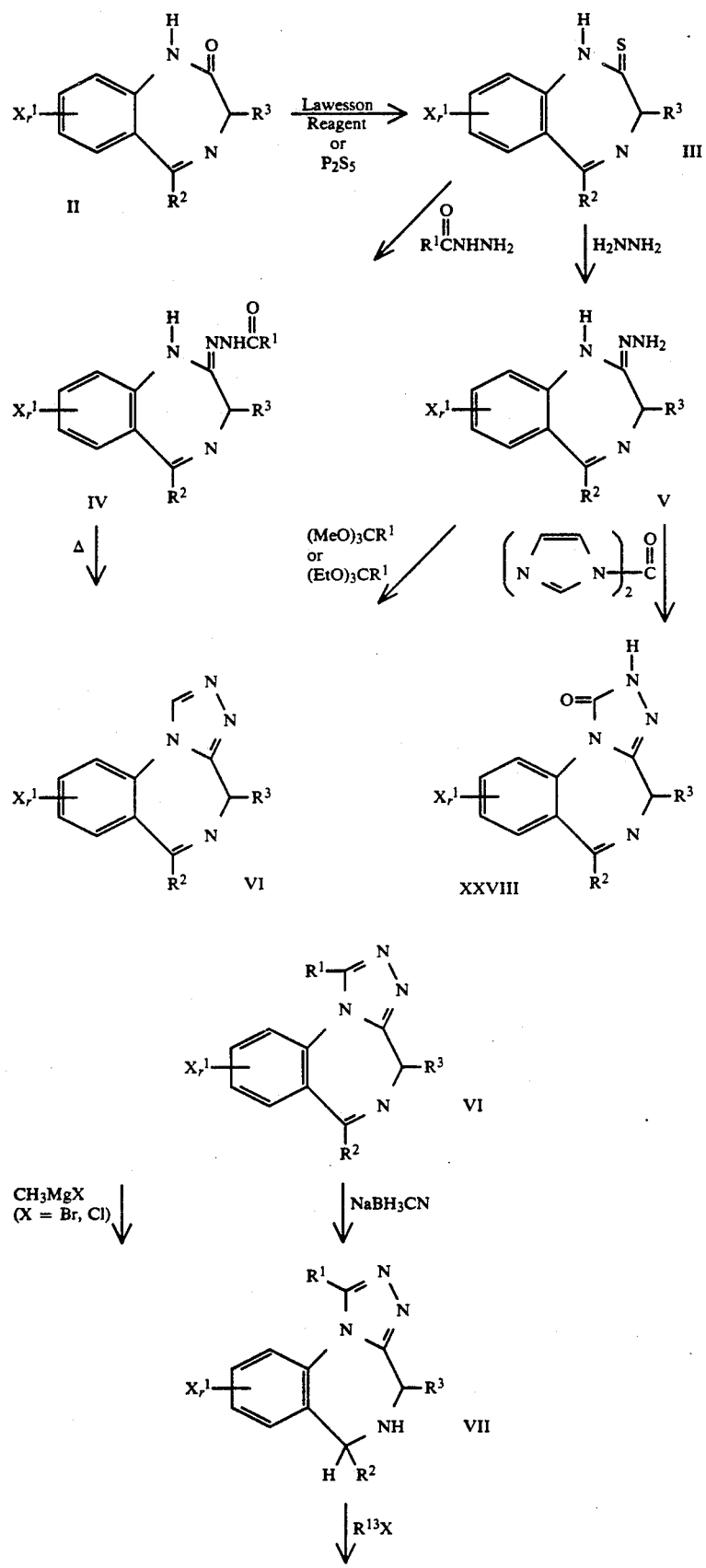

-continued
REACTION SCHEME I
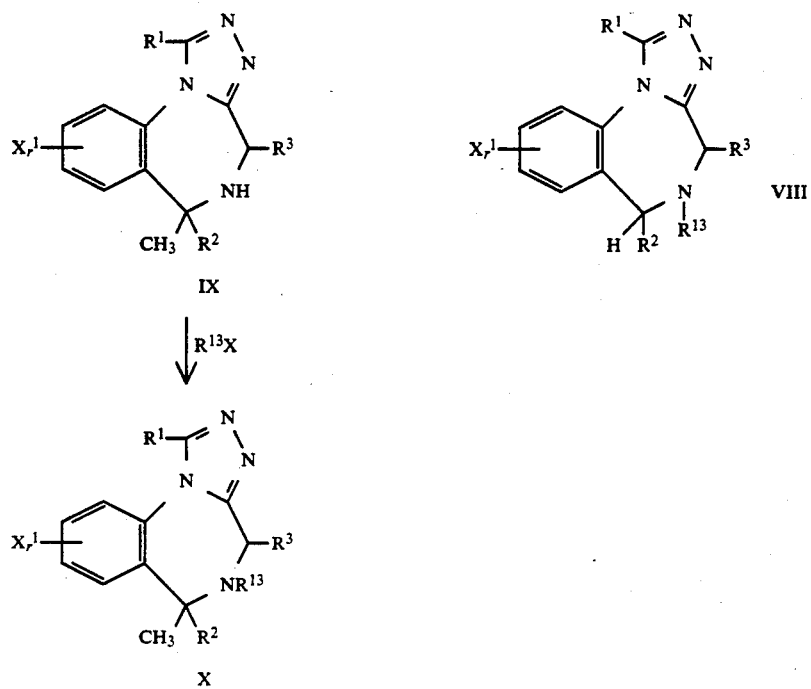
X=halo where $R^{13}$ is alkyl or substituted alkyl,
X=halo, O where $R^{13}$ is acyl
REACTION SCHEME II
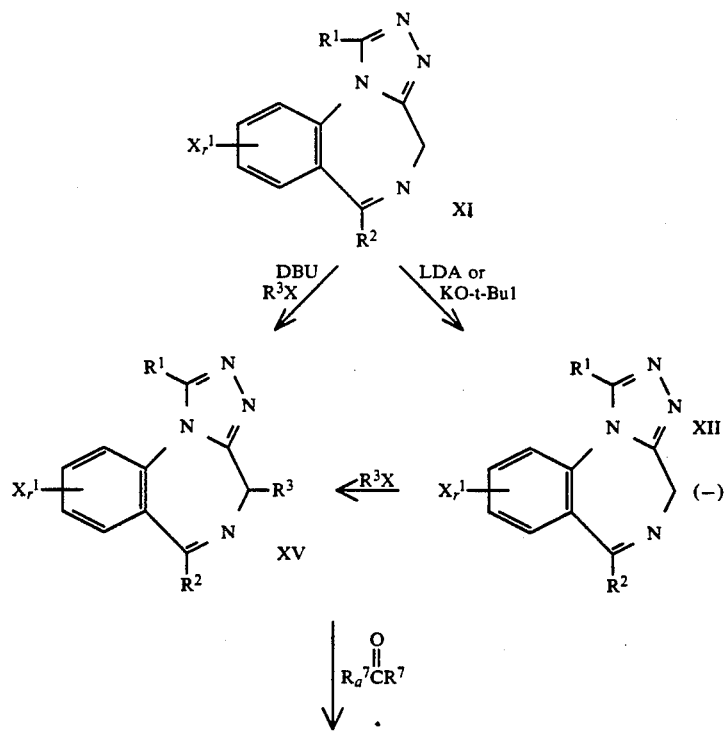

REACTION SCHEME II
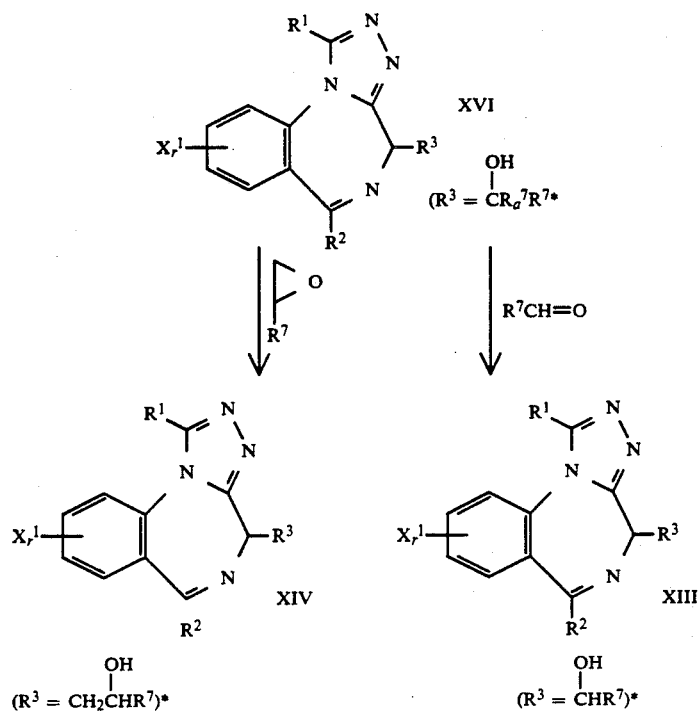
n is at least 1 where the attachment atom of to R$^7$ is C; otherwise n is at least 2)
*(except where the attachment atom of R$^7$ is other than C)
REACTION SCHEME III
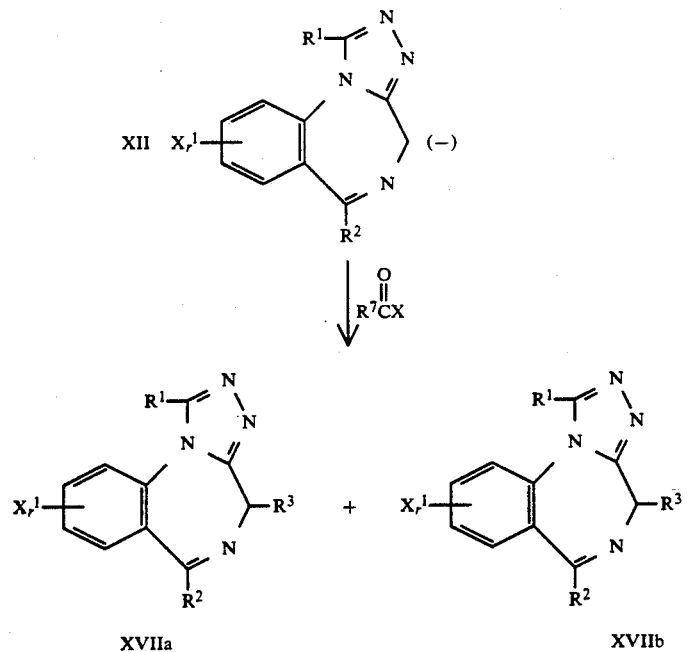
or (if peroxide present)

REACTION SCHEME III
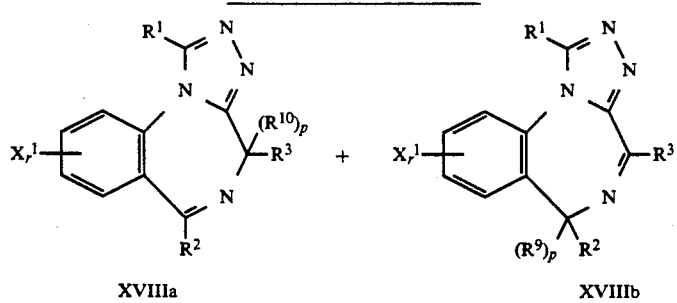
(except where atom adjacent to R⁷ is other than C)
REACTION SCHEME IV
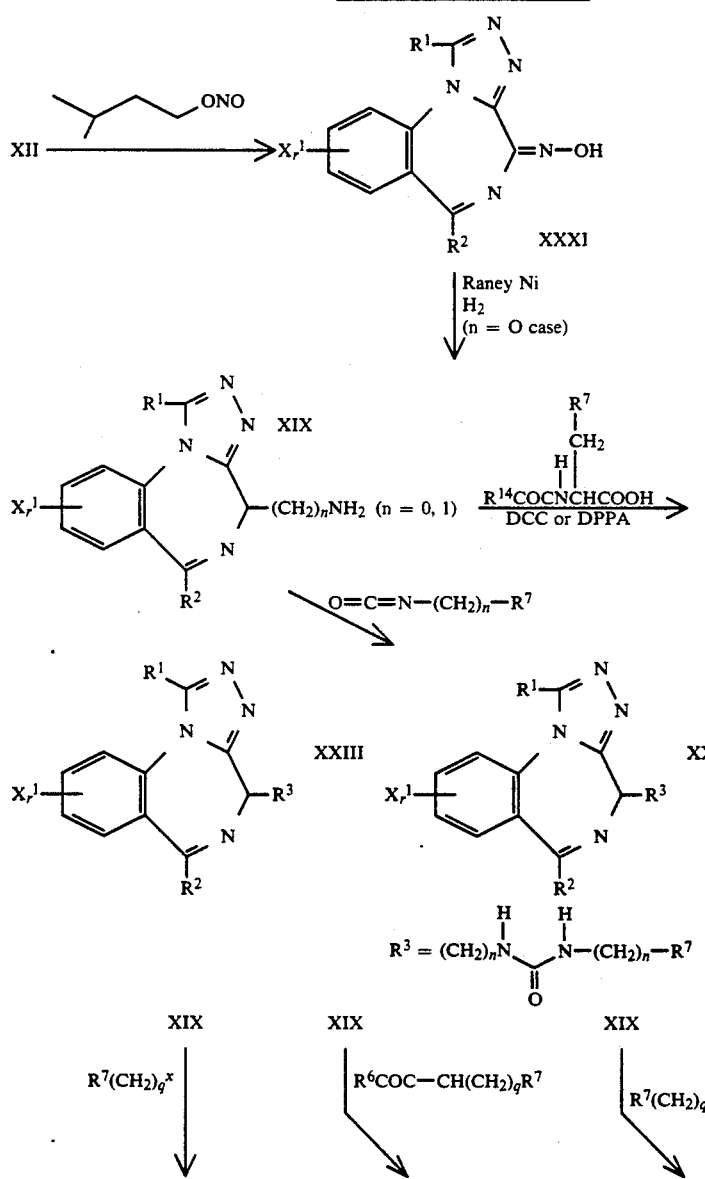

-continued
REACTION SCHEME IV
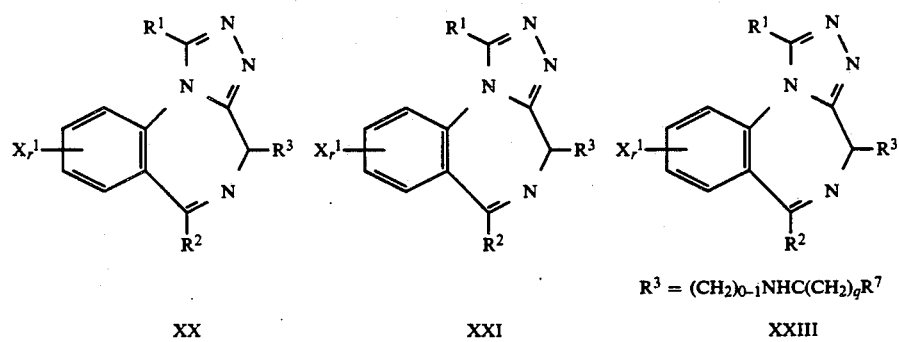
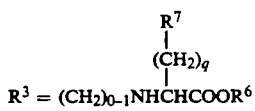
REACTION SCHEME V
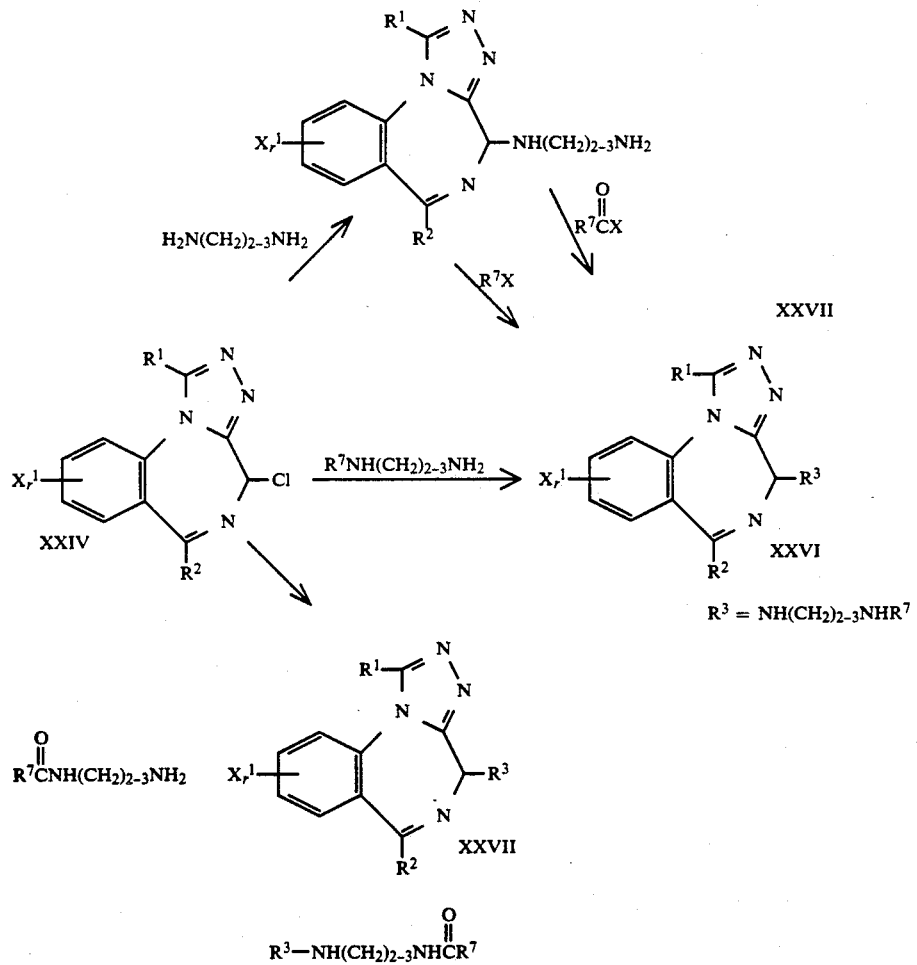

REACTION SCHEME Va

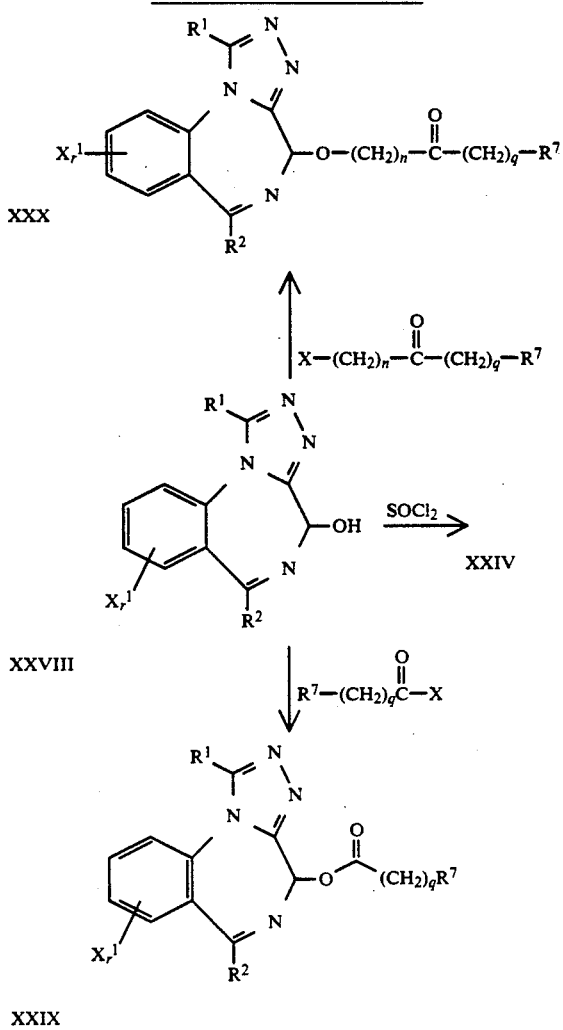

Referring to Reaction Scheme I, the benzodiazepinones of Formula II are reacted with Lawesson's reagent

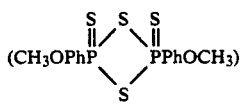

in an organic solvent and heated at reflux in an inert atomosphere. Upon cooling, the reaction mixture is separated, as by silica gel chromatography, to produce the benzodiazepinethione (III).

The triazolobenzodiazepines (VI) can be generated from III by either 1) reacting III with hydrazine to produce the benzodiazepinehydrazone (V) which is then combined with a trialkylorthoester at acidic pH, or 2) reacting III with an acylhydrazide in a heated organic solvent to produce the acylamidrazone IV which is then heated to produce VI. Compound V is also converted to XXVIII by treatament with carbonyldiimidazole.

VI is stirred in acetic acid at 10° C. and treated with sodium cyanoborohydride. The mixture is stirred from 5 to 60 minutes, preferably 5 minutes, and the reaction monitored by thin layer chromatography (tlc). The mixture is diluted with cold water, made basic and extracted with organic solvents. The organic layers are combined, washed with brine, dried over sodium sulfate, filtered, and evaporated to dryness in vacuo and the residue is purified by column chromatography on silica gel or by recrystallization to give 5,6-dihydrobenzodiazepines VII.

The compound VII in methylene chloride is treated with an excess of an acyl halide or anhydride, e.g. benzoyl chloride or acetic anhydride, or an alkyl halide, e.g. methyl iodide or ethyl bromide, and stirred at room temperature. With acyl halides or anhydrides, a base such as triethyl amine or 4-dimethylaminopyridine is added as a catalyst. Upon completion of the reaction (1-92 hrs), the mixture is diluted with water and separated. The organic layer is washed with water, sodium carbonate, dried filtered, and evaporated. The residue is purified by recrystallization or by column chromatography on silica gel to give 5-alkyl- and 5-acyl-5,6-dihydro-4H-s-triazolo [4,3-a]-1,4-benzodiazepines, VIII.

Alternatively, IV is treated with a Grignard reagent to yield the amine IX, which is then reacted analogously to VII to yield the N-alkyl or N-acyl analog X.

Referring now to Reaction Scheme II, the anion XII is generated from XI by the procedure of J. Org. Chem., 46, 3945 (1981) using lithium diisopropylamide (LDA) or using potassium tert-butoxide.

XII can be variously treated. For example, the hydroxy alkyl derivative XIII is generated by adding an aldehyde to a solution of XII. Treatment of XII with an epoxide yields the hydroxyethyl derivative XIV. By treating XII with an alkyl halide, the alkyl derivative XV is produced. Lastly, the hydroxy alkyl compound XVI is derived from treatment of XII with a ketone.

An alternative procedure for obtaining XV is to treat XI with an alkyl halide and a strong base such as 1,8-diazabicyclo[5.4.0]undec-7-ene (DBU) and heating.

These procedures also produce isomers of XIII-XVI which are analogous to XVIIb (Reaction Scheme III). Likewise, in the presence of peroxide, the analogs of the isomers and hydroxy derivatives XVIIIa and XVIIIb are produced.

Reaction Scheme III describes the formation of $R^3$=keto compounds of Formula I. These are produced by treating the anion XII with an acid halide or anhydride. This reaction produces both isomers XVIIa and XVIIb. When the reaction is run in the presence of peroxide, the hydroxy compounds XVIIIa and XVIIIb are produced.

Reaction Scheme IV describes the formation of Formula I compounds where $R^3$ is a substituted amino or aminomethyl.

The triazolobenzodiazepines XIX are either known or readily derivable from known compounds. The former compound may also be obtained by nitrosation of XII followed by reduction of the oxime XXXI with Raney nickel and hydrogen.

When XIX is treated with an alkyl halide, the N-alkyl derivative XX is produced.

When XIX is treated with an alpha-halo carboxylic acid derivative such as an a-halo acid, ester, amide, or the like, one obtains the corresponding a-amino compound XXI.

Treatment of XIX with an acid halide or anhydride produces the N-acyl derivative XXII.

Compound XIX may also be treated with an N-protected a-amino acid and a coupling reagent such as DCC or DPPA (diphenylphosphorylazide) to give the amides of structure XXIII.

Treatment of Compound XIX with an isocyanate gives the ureas XXXII.

Referring now to Reaction Schemes V/Va, the 4-hydroxy-triazolobenzolodiazepine (XXVIII) is treated with thionyl chloride to give the 4-chloro-triazobenzodiazepine XXIV. The chloride is treated with an excess amount of ethylene or propylene diamine to yield the substituted diamine XXV. XXV can be reacted with an alkyl halide to yield the alkyl derivative XXVI. XXVI can also be directly derived from XXIV by treatment of XXIV with a monoalkyl ethylene or propylene diamine. The hydroxy compound (XXVIII) may also be either acylated or alkylated to give (XXVIII) and (XXX) respectively.

Treatment of XXIV with an acid halide or anhydride produces the N-acyl diamine XXVII, which can also be directly produced from XXIV by treatment of XXIV with a monoacyl ethylene or propylene diamine.

In cases where the starting materials are optically active, the chirality at $C_4$ is controlled by the synthesis. When racemic starting materials are employed, racemic products are obtained. The enantiomers may be separated by resolution.

In Vitro Activity of Formula I

The biological activity of the compounds of Formula I have been evaluated using 1) an $^{125}$I-CCK receptor binding assay and in vitro isolated tissue preparations and 2) $^{125}$I-gastrin and $^3$H-pentagastrin binding assays.

Materials and Methods

1. CCK receptor binding (pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor binding was performed according to Innis and Snyder (*Proc. Natl. Acad. Sci.* 77: 6917-6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200-350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

2. CCK Receptor Binding (Brain)

CCK-33 was radiolabeled and the binding was performed according to the description for the pancreas method with modification according to Saito et al. (*J. Neurochem.* 37, 483-490, 1981).

Male Hartley guinea pigs (300-500 g) were sacrificed by decapitation and the brains were removed and placed in ice-cold 50 mM, Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris Trizma buffer with a Brinkman polytron PT-10. The homogenates were centrifuged at 42,000 g for 15 min. Pellets were resuspended in Tris Buffer, centrifuged as above and resuspended in 200 volumes of binding assay buffer (10 mM N-2-hydroxethyl-piperazine-N'-2-ethane sulfonic acid (HEPES), 5 mM $MgCl_2$, 0.25 mg/ml bacitracin, 1 mM ethylene glycol-bis-(β-aminoethylether-N,N'-tetra-acetic acid (EGTA), and 0.4% bovine serum albumin (BSA)). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400-600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions are recorded using Statham (60 g; 0.12 mm) strain gauges and a Hewlett-Packard (77588) recorder. The tissues are washed every 10 minutes for 1 hr to obtain equilibrium prior to the beginning of the study. CCK-8 is added cumulatively to the baths and $EC_{50}$'s determined using regression analysis. After washout (every 10 minutes for 1 hr), the compound of Formula I is added at least 5 minutes before the addition of CCK-8 and the $EC_{50}$ of CCK-8 in the presence of the compound of Formula I similarly determined.

4. Isolated longitudinal muscle of guinea pig ileum

Longitudinal muscle strips with attached nerve plexus are prepared as described in *Brit J. Pharmac.* 23: ; 356-363, 1964; *J. Physiol.* 194: 13-33, 1969. Male Hartley guinea pigs are decapitated and the ileum is removed (10 cm of the terminal ileum is discarded and the adjacent 20 cm piece is used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds of Formula I determined as described in the gall bladder protocol (above).

Gastrin Antagonism

Gastrin antagonist activity of compounds of Formula I is determined using the following assay:

Gastrin Receptor Binding in Guinea Pig Gastric Glands
Preparation of guinea pig gastric mucosal glands Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300–500 g body weight, male Hartley) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

Binding Studies

The washed guinea pig gastric glands prepared as above were resuspended in 25 ml of standard buffer containing 0.25 mg/ml of bacitracin. For binding studies, to 220 μl of gastric glands in triplicate tubes, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}$I-gastrin or liquid scintillation counting for $^3$H-pentagastrin.

Representative Formula I compounds were assayed and found to have gastrin inhibiting activity.

In Vitro Results

1. Effect of the Compounds of Formula I on $^{125}$I-CCK-33 Receptor Binding

The preferred compounds of Formula I inhibited specific $^{125}$I-CCK-33 binding in a concentration dependent manner.

Scatchard analysis of specific $^{125}$I-CCK-33 receptor binding in the absence and presence of the compounds of Formula I indicated the compounds of Formula I competitively inhibited specific $^{125}$I-CCK-33 receptor binding since it increased the $K_D$ (dissociation constant) without affecting the $B_{MAX}$ (maximum receptor number). A $K_i$ value (dissociation constant of inhibitor) of the compounds of Formula I was estimated.

The data of Table 1 were obtained for compounds of the following formula:

| Formula IA Compound No. | $R^1$ | $R^{3'}$ |
|---|---|---|
| 1 | H | —$CH_2$-indol-3-yl |
| 2 | $CH_3$ | —$CH_2$-indol-3-yl |
| 3 | phenyl | —$CH_2$-indol-3-yl |
| 4 | —$CH_2$—$N(CH_3)_2$ | —$CH_2$-indol-3-yl |
| 5 | OH | —$CH_2$-indol-3-yl |
| 6 | $CCl_3$ | —$CH_2$-indol-3-yl |
| 7 | H | —NH—CO—O$CH_2$-phenyl |
| 8 | H | —NH—CO-4-chlorophenyl |
| 9 | H | —NH—CO-indol-2-yl |
| 10 | $CH_3$ | —NH—CO-indol-2-yl |
| 11 | H | —NH—CO—NH-4-Chlorophenyl |
| 12 | $CH_3$ | —NH—CO—NH-4-Chlorophenyl |

TABLE 1
CCK Receptor Binding Results

| Formula IA Compound No. | $IC_{50}(\mu M)$ $^{125}$I-CCK Pancreas | $^{125}$I-CCK Brain |
|---|---|---|
| 1 | 0.2 | 100 |
| 2 | 0.3 | 38.6 |
| 3 | 22 | 100 |
| 4 | 14 | 100 |
| 5 | 3.1 | 63 |
| 6 | 25 | 100 |
| 7 | 0.22 | 8 |
| 8 | 0.0044 | 9.3 |
| 9 | 0.0009 | 0.053 |
| 10 | 0.0004 | 0.066 |
| 11 | 0.12 | 0.48 |
| 12 | 0.082 | 0.08 |

Preferred compounds of Formula I are those of the series where $R^1$ is H, methyl, carboxyl, carboxyethyl, carboxymethyl, or trifluoromethyl.

Other series of preferred compounds are those where $R^2$ is phenyl, p-chlorophenyl, o-fluorophenyl, o-chlorophenyl, p-fluorophenyl, 2,4-dichlorophenyl, 2,6-difluorophenyl, —$CH_2$COO-t-butyl, or —$CH_2$COOEt.

Other series of preferred compounds are those where $R^3$ is 2- or 3-indolylmethyl, CO-2-(1-methyl-indolyl), CO-3-(1-methylindolyl), —CO-thiophene, —CHOH-1-methylindol-3-yl, NHCONH-p-Cl-phenyl, NHCO-$R^7$ where $R^7$ is 2-indolyl, 2-(1-methyl-indolyl), 2-(5-F-indolyl), -2-benzofuranyl, -2-benzothienyl, -2-(3-methylindenyl), cinnamoyl, mono- or dihalo phenyl, mono- or dimethyl or trifluoromethyl phenyl.

When p is 1 for any of $R^9$, $R^{10}$ or $R^{13}$, it is preferred that $R^9$ is H or hydroxyl, $R^{10}$ is H or hydroxyl, and $R^{13}$ is H.

It is preferred that $X^1_r$ is H, Cl, F, $CF_3$, OH; or $NO_2$.

Examples of Formula I compounds are tabulated below.

TABLE 2

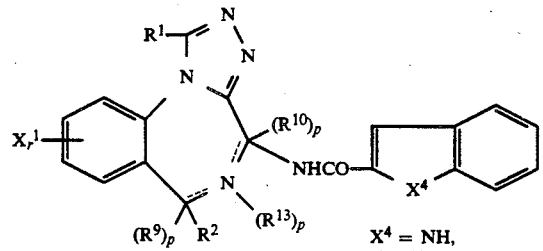

$X^4$ = NH, N—$CH_3$, O, or S

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 3

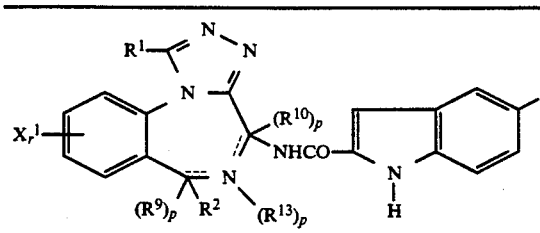

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |

TABLE 3-continued

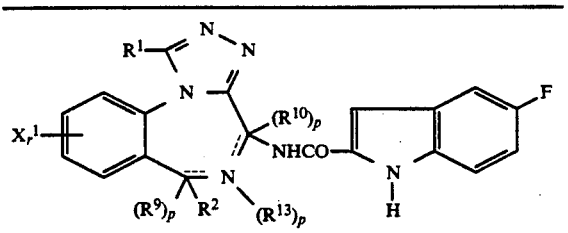

| X¹ | r | R¹ | (R⁹)ₚ | R² | (R¹³)ₚ | (R¹⁰)ₚ |
|---|---|---|---|---|---|---|
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 4

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |

TABLE 4-continued

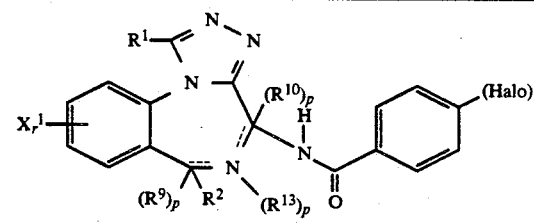

| X¹ | r | R¹ | (R⁹)ₚ | R² | (R¹³)ₚ | (R¹⁰)ₚ |
|---|---|---|---|---|---|---|
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |

TABLE 4-continued

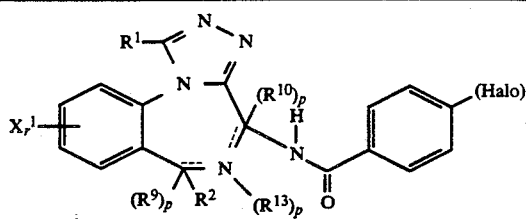

| X¹ | r | R¹ | (R⁹)ₚ | R² | (R¹³)ₚ | (R¹⁰)ₚ |
|---|---|---|---|---|---|---|
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 5

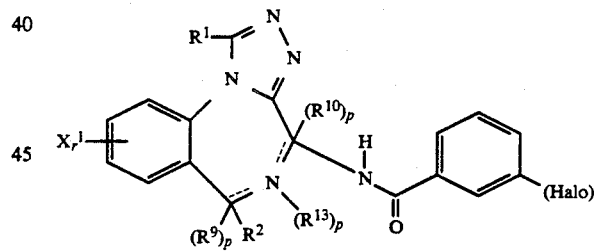

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |

TABLE 5-continued

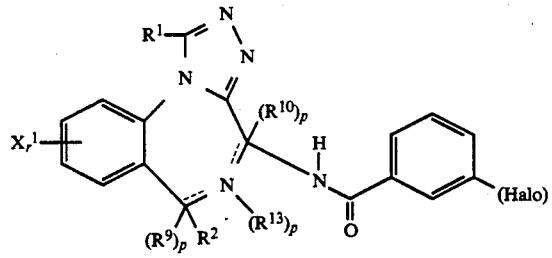

| X¹ | r | R¹ | (R⁹)ₚ | R² | (R¹³)ₚ | (R¹⁰)ₚ |
|---|---|---|---|---|---|---|
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |

TABLE 5-continued

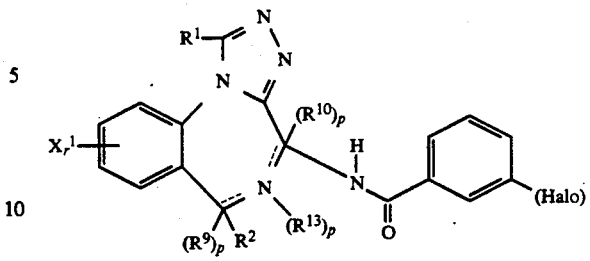

| X¹ | r | R¹ | (R⁹)ₚ | R² | (R¹³)ₚ | (R¹⁰)ₚ |
|---|---|---|---|---|---|---|
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 6

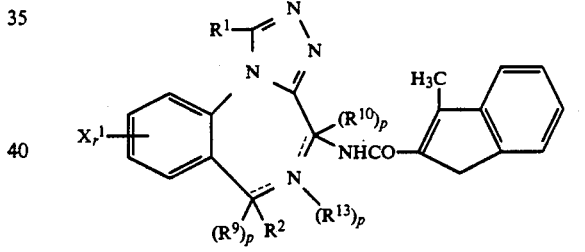

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |

TABLE 6-continued

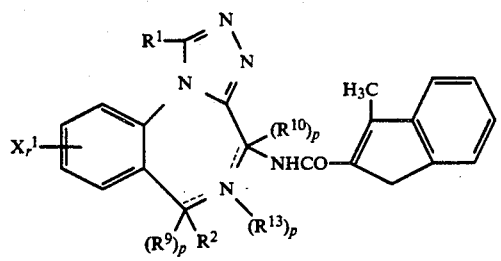

| $X^1$ | r | $R^1$ | $(R^9)_p$ | $R^2$ | $(R^{13})_p$ | $(R^{10})_p$ |
|---|---|---|---|---|---|---|
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |

TABLE 6-continued

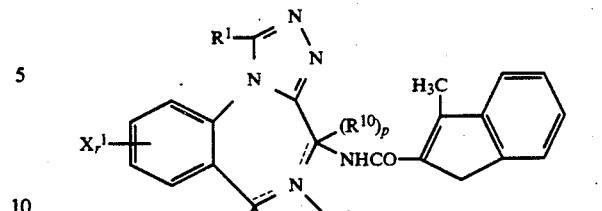

| $X^1$ | r | $R^1$ | $(R^9)_p$ | $R^2$ | $(R^{13})_p$ | $(R^{10})_p$ |
|---|---|---|---|---|---|---|
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 7

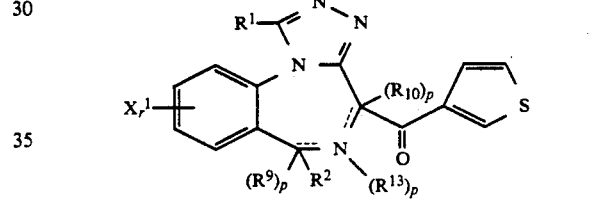

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |

TABLE 7-continued

| X¹ | r | R¹ | (R⁹)$_p$ | R² | (R¹³)$_p$ | (R¹⁰)$_p$ |
|---|---|---|---|---|---|---|
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CF₃ | — | Ph | — | OH |
| H | 1 | COOH | — | Ph | — | OH |
| H | 1 | CH₃ | — | o-F—Ph | — | OH |
| H | 1 | CF₃ | — | o-F—Ph | — | OH |
| H | 1 | COOH | — | o-F—Ph | — | OH |
| H | 1 | CH₃ | — | CH₂COOt-Bu | — | OH |
| H | 1 | CF₃ | — | CH₂COOt-Bu | — | OH |
| H | 1 | COOH | — | CH₂COOt-Bu | — | OH |

TABLE 8

| X¹ | r | R¹ | (R⁹)$_p$ | R² | (R¹³)$_p$ | (R¹⁰)$_p$ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |

TABLE 8-continued structure: R¹-triazole fused with phenyl ring bearing X¹ᵣ, (R⁹)ₚ R², (R¹³)ₚ substituents, with (R¹⁰)ₚ and NHCO-CH=CH-Ph group

| X¹ | r | R¹ | (R⁹)ₚ | R² | (R¹³)ₚ | (R¹⁰)ₚ |
|---|---|---|---|---|---|---|
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 9 structure: R¹-triazole fused with phenyl ring bearing X¹ᵣ, (R⁹)ₚ R², (R¹³)ₚ substituents, with (R¹⁰)ₚ and NHCONH-Ph(Halo) group

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |

TABLE 9-continued

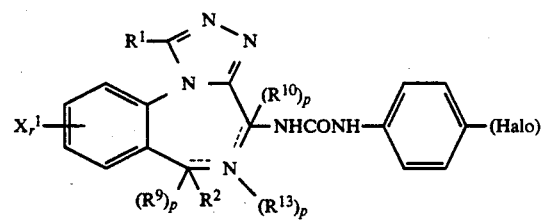

| $X^1$ | r | $R^1$ | $(R^9)_p$ | $R^2$ | $(R^{13})_p$ | $(R^{10})_p$ |
|---|---|---|---|---|---|---|
| OH | 1 | H | — | p-Cl—Ph | — | H |
| H | 1 | CH$_3$ | — | p-Cl—Ph | — | H |
| F | 1 | CH$_3$ | — | p-Cl—Ph | — | H |
| CF$_3$ | 1 | CH$_3$ | — | p-Cl—Ph | — | H |
| OH | 1 | CH$_3$ | — | p-Cl—Ph | — | H |
| H | 1 | COOH | — | p-Cl—Ph | — | H |
| F | 1 | COOH | — | p-Cl—Ph | — | H |
| CF$_3$ | 1 | COOH | — | p-Cl—Ph | — | H |
| OH | 1 | COOH | — | p-Cl—Ph | — | H |
| H | 1 | CF$_3$ | — | p-Cl—Ph | — | H |
| H | 1 | CH$_2$COOH | — | p-Cl—Ph | — | H |
| H | 1 | CH$_2$CH$_2$COOH | — | p-Cl—Ph | — | H |
| H | 1 | H | — | CH$_2$COOt-Bu | — | H |
| Cl | 1 | H | — | CH$_2$COOt-Bu | — | H |
| F | 1 | H | — | CH$_2$COOt-Bu | — | H |
| CF$_3$ | 1 | H | — | CH$_2$COOt-Bu | — | H |
| OH | 1 | H | — | CH$_2$COOt-Bu | — | H |
| NO$_2$ | 1 | H | — | CH$_2$COOt-Bu | — | H |
| H | 1 | CH$_3$ | — | CH$_2$COOt-Bu | — | H |
| Cl | 1 | CH$_3$ | — | CH$_2$COOt-Bu | — | H |
| F | 1 | CH$_3$ | — | CH$_2$COOt-Bu | — | H |
| CF$_3$ | 1 | CH$_3$ | — | CH$_2$COOt-Bu | — | H |
| OH | 1 | CH$_3$ | — | CH$_2$COOt-Bu | — | H |
| NO$_2$ | 1 | CH$_3$ | — | CH$_2$COOt-Bu | — | H |
| H | 1 | COOH | — | CH$_2$COOt-Bu | — | H |
| Cl | 1 | COOH | — | CH$_2$COOt-Bu | — | H |
| F | 1 | COOH | — | CH$_2$COOt-Bu | — | H |
| CF$_3$ | 1 | COOH | — | CH$_2$COOt-Bu | — | H |
| OH | 1 | COOH | — | CH$_2$COOt-Bu | — | H |
| NO$_2$ | 1 | COOH | — | CH$_2$COOt-Bu | — | H |
| H | 1 | CF$_3$ | — | CH$_2$COOt-Bu | — | H |
| OH | 1 | CF$_3$ | — | CH$_2$COOt-Bu | — | H |
| H | 1 | CH$_2$COOH | — | CH$_2$COOt-Bu | — | H |
| OH | 1 | CH$_2$COOH | — | CH$_2$COOt-Bu | — | H |
| H | 1 | CH$_2$CH$_2$COOH | — | CH$_2$COOt-Bu | — | H |
| OH | 1 | CH$_2$CH$_2$COOH | — | CH$_2$COOt-Bu | — | H |
| H | 1 | H | — | CH$_2$COOEt | — | H |
| Cl | 1 | H | — | CH$_2$COOEt | — | H |
| F | 1 | H | — | CH$_2$COOEt | — | H |
| CF$_3$ | 1 | H | — | CH$_2$COOEt | — | H |
| OH | 1 | H | — | CH$_2$COOEt | — | H |
| NO$_2$ | 1 | H | — | CH$_2$COOEt | — | H |
| H | 1 | CH$_3$ | — | CH$_2$COOEt | — | H |
| Cl | 1 | CH$_3$ | — | CH$_2$COOEt | — | H |
| F | 1 | CH$_3$ | — | CH$_2$COOEt | — | H |
| CF$_3$ | 1 | CH$_3$ | — | CH$_2$COOEt | — | H |
| OH | 1 | CH$_3$ | — | CH$_2$COOEt | — | H |
| NO$_2$ | 1 | CH$_3$ | — | CH$_2$COOEt | — | H |
| H | 1 | COOH | — | CH$_2$COOEt | — | H |
| Cl | 1 | COOH | — | CH$_2$COOEt | — | H |
| F | 1 | COOH | — | CH$_2$COOEt | — | H |
| CF$_3$ | 1 | COOH | — | CH$_2$COOEt | — | H |
| OH | 1 | COOH | — | CH$_2$COOEt | — | H |
| NO$_2$ | 1 | COOH | — | CH$_2$COOEt | — | H |
| H | 1 | CF$_3$ | — | CH$_2$COOEt | — | H |
| OH | 1 | CF$_3$ | — | CH$_2$COOEt | — | H |
| H | 1 | CH$_2$COOH | — | CH$_2$COOEt | — | H |
| OH | 1 | CH$_2$COOH | — | CH$_2$COOEt | — | H |
| H | 1 | CH$_2$CH$_2$COOH | — | CH$_2$COOEt | — | H |
| OH | 1 | CH$_2$CH$_2$COOH | — | CH$_2$COOEt | — | H |

TABLE 10

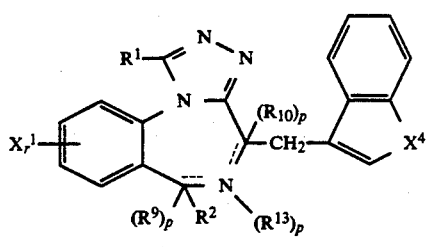

$X_4$ = NH, NCH$_3$, O, or S

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| CF$_3$ | 1 | H | — | Ph | — | H |
| OH | 1 | H | — | Ph | — | H |
| NO$_2$ | 1 | H | — | Ph | — | H |
| H | 1 | CH$_3$ | — | Ph | — | H |
| Cl | 1 | CH$_3$ | — | Ph | — | H |
| F | 1 | CH$_3$ | — | Ph | — | H |
| CF$_3$ | 1 | CH$_3$ | — | Ph | — | H |
| OH | 1 | CH$_3$ | — | Ph | — | H |
| NO$_2$ | 1 | CH$_3$ | — | Ph | — | H |
| H | 1 | COOH | — | Ph | — | H |
| Cl | 1 | COOH | — | Ph | — | H |
| F | 1 | COOH | — | Ph | — | H |
| CF$_3$ | 1 | COOH | — | Ph | — | H |
| OH | 1 | COOH | — | Ph | — | H |
| NO$_2$ | 1 | COOH | — | Ph | — | H |
| H | 1 | CF$_3$ | — | Ph | — | H |
| OH | 1 | CF$_3$ | — | Ph | — | H |
| H | 1 | CH$_2$COOH | — | Ph | — | H |
| OH | 1 | CH$_2$COOH | — | Ph | — | H |
| H | 1 | CH$_2$CH$_2$COOH | — | Ph | — | H |
| OH | 1 | CH$_2$CH$_2$COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF$_3$ | 1 | H | — | o-F—Ph | — | H |
| OH | 1 | H | — | o-F—Ph | — | H |
| NO$_2$ | 1 | H | — | o-F—Ph | — | H |
| H | 1 | CH$_3$ | — | o-F—Ph | — | H |
| Cl | 1 | CH$_3$ | — | o-F—Ph | — | H |
| F | 1 | CH$_3$ | — | o-F—Ph | — | H |
| CF$_3$ | 1 | CH$_3$ | — | o-F—Ph | — | H |
| OH | 1 | CH$_3$ | — | o-F—Ph | — | H |
| NO$_2$ | 1 | CH$_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF$_3$ | 1 | COOH | — | o-F—Ph | — | H |
| OH | 1 | COOH | — | o-F—Ph | — | H |
| NO$_2$ | 1 | COOH | — | o-F—Ph | — | H |
| H | 1 | CF$_3$ | — | o-F—Ph | — | H |
| OH | 1 | CF$_3$ | — | o-F—Ph | — | H |
| H | 1 | CH$_2$COOH | — | o-F—Ph | — | H |
| OH | 1 | CH$_2$COOH | — | o-F—Ph | — | H |
| H | 1 | CH$_2$CH$_2$COOH | — | o-F—Ph | — | H |
| OH | 1 | CH$_2$CH$_2$COOH | — | o-F—Ph | — | H |
| H | 1 | H | — | p-Cl—Ph | — | H |
| F | 1 | H | — | p-Cl—Ph | — | H |
| CF$_3$ | 1 | H | — | p-Cl—Ph | — | H |
| OH | 1 | H | — | p-Cl—Ph | — | H |
| H | 1 | CH$_2$ | — | p-Cl—Ph | — | H |
| F | 1 | CH$_3$ | — | p-Cl—Ph | — | H |
| CF$_3$ | 1 | CH$_3$ | — | p-Cl—Ph | — | H |
| OH | 1 | CH$_3$ | — | p-Cl—Ph | — | H |
| H | 1 | COOH | — | p-Cl—Ph | — | H |
| F | 1 | COOH | — | p-Cl—Ph | — | H |
| CF$_3$ | 1 | COOH | — | p-Cl—Ph | — | H |
| OH | 1 | COOH | — | p-Cl—Ph | — | H |
| H | 1 | CF$_3$ | — | p-Cl—Ph | — | H |
| H | 1 | CH$_2$COOH | — | p-Cl—Ph | — | H |
| H | 1 | CH$_2$CH$_2$COOH | — | p-Cl—Ph | — | H |
| H | 1 | H | — | CH$_2$COOt-Bu | — | H |
| Cl | 1 | H | — | CH$_2$COOt-Bu | — | H |
| F | 1 | H | — | CH$_2$COOt-Bu | — | H |
| CF$_3$ | 1 | H | — | CH$_2$COOt-Bu | — | H |

TABLE 10-continued

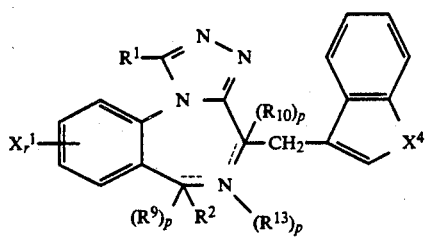

X4 = NH, NCH3, O, or S

| X¹ | r | R¹ | (R⁹)p | R² | (R¹³)p | (R¹⁰)p |
|---|---|---|---|---|---|---|
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CF₃ | — | Ph | — | OH |
| H | 1 | COOH | — | Ph | — | OH |
| H | 1 | CH₃ | — | o-F—Ph | — | OH |
| H | 1 | CF₃ | — | o-F—Ph | — | OH |
| H | 1 | COOH | — | o-F—Ph | — | OH |
| H | 1 | CH₃ | — | CH₂COOt-Bu | — | OH |
| H | 1 | CF₃ | — | CH₂COOt-Bu | — | OH |
| H | 1 | COOH | — | CH₂COOt-Bu | — | OH |

TABLE 11

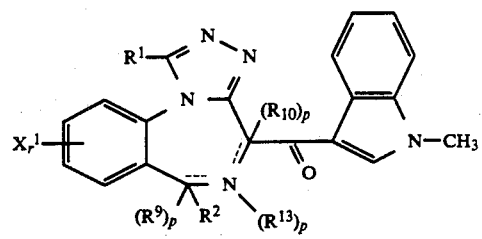

| X¹ | r | R¹ | (R⁹)p | R² | (R¹³)p | (R¹⁰)p |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |

TABLE 11-continued

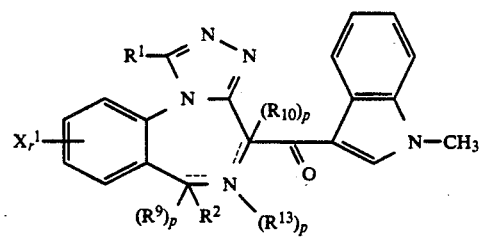

| X¹ | r | R¹ | (R⁹)p | R² | (R¹³)p | (R¹⁰)p |
|---|---|---|---|---|---|---|
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CF₃ | — | Ph | — | OH |
| H | 1 | COOH | — | Ph | — | OH |
| H | 1 | CH₃ | — | o-F—Ph | — | OH |
| H | 1 | CF₃ | — | o-F—Ph | — | OH |
| H | 1 | COOH | — | o-F—Ph | — | OH |
| H | 1 | CH₃ | — | CH₂COOt-Bu | — | OH |
| H | 1 | CF₃ | — | CH₂COOt-Bu | — | OH |
| H | 1 | COOH | — | CH₂COOt-Bu | — | OH |

TABLE 12

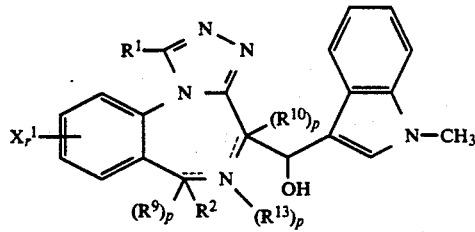

| X¹ | r | R¹ | (R⁹)p | R² | (R¹³)p | (R¹⁰)p |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |

TABLE 12-continued

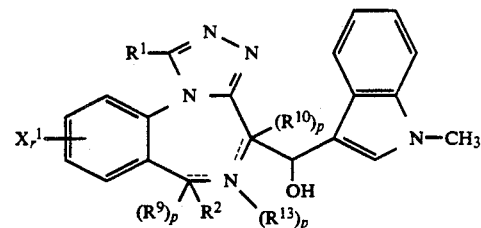

| X¹ | r | R¹ | (R⁹)$_p$ | R² | (R¹³)$_p$ | (R¹⁰)$_p$ |
|---|---|---|---|---|---|---|
| H | 1 | CH$_3$ | — | CH$_2$COOt-Bu | — | H |
| Cl | 1 | CH$_3$ | — | CH$_2$COOt-Bu | — | H |
| F | 1 | CH$_3$ | — | CH$_2$COOt-Bu | — | H |
| CF$_3$ | 1 | CH$_3$ | — | CH$_2$COOt-Bu | — | H |
| OH | 1 | CH$_3$ | — | CH$_2$COOt-Bu | — | H |
| NO$_2$ | 1 | CH$_3$ | — | CH$_2$COOt-Bu | — | H |
| H | 1 | COOH | — | CH$_2$COOt-Bu | — | H |
| Cl | 1 | COOH | — | CH$_2$COOt-Bu | — | H |
| F | 1 | COOH | — | CH$_2$COOt-Bu | — | H |
| CF$_3$ | 1 | COOH | — | CH$_2$COOt-Bu | — | H |
| OH | 1 | COOH | — | CH$_2$COOt-Bu | — | H |
| NO$_2$ | 1 | COOH | — | CH$_2$COOt-Bu | — | H |
| H | 1 | CF$_3$ | — | CH$_2$COOt-Bu | — | H |
| OH | 1 | CF$_3$ | — | CH$_2$COOt-Bu | — | H |
| H | 1 | CH$_2$COOH | — | CH$_2$COOt-Bu | — | H |
| OH | 1 | CH$_2$COOH | — | CH$_2$COOt-Bu | — | H |
| H | 1 | CH$_2$CH$_2$COOH | — | CH$_2$COOt-Bu | — | H |
| OH | 1 | CH$_2$CH$_2$COOH | — | CH$_2$COOt-Bu | — | H |
| H | 1 | H | — | CH$_2$COOEt | — | H |
| Cl | 1 | H | — | CH$_2$COOEt | — | H |
| F | 1 | H | — | CH$_2$COOEt | — | H |
| CF$_3$ | 1 | H | — | CH$_2$COOEt | — | H |
| OH | 1 | H | — | CH$_2$COOEt | — | H |
| NO$_2$ | 1 | H | — | CH$_2$COOEt | — | H |
| H | 1 | CH$_3$ | — | CH$_2$COOEt | — | H |
| Cl | 1 | CH$_3$ | — | CH$_2$COOEt | — | H |
| F | 1 | CH$_3$ | — | CH$_2$COOEt | — | H |
| CF$_3$ | 1 | CH$_3$ | — | CH$_2$COOEt | — | H |
| OH | 1 | CH$_3$ | — | CH$_2$COOEt | — | H |
| NO$_2$ | 1 | CH$_3$ | — | CH$_2$COOEt | — | H |
| H | 1 | COOH | — | CH$_2$COOEt | — | H |
| Cl | 1 | COOH | — | CH$_2$COOEt | — | H |
| F | 1 | COOH | — | CH$_2$COOEt | — | H |
| CF$_3$ | 1 | COOH | — | CH$_2$COOEt | — | H |
| OH | 1 | COOH | — | CH$_2$COOEt | — | H |
| NO$_2$ | 1 | COOH | — | CH$_2$COOEt | — | H |
| H | 1 | CF$_3$ | — | CH$_2$COOEt | — | H |
| OH | 1 | CF$_3$ | — | CH$_2$COOEt | — | H |
| H | 1 | CH$_2$COOH | — | CH$_2$COOEt | — | H |
| OH | 1 | CH$_2$COOH | — | CH$_2$COOEt | — | H |
| H | 1 | CH$_2$CH$_2$COOH | — | CH$_2$COOEt | — | H |
| OH | 1 | CH$_2$CH$_2$COOH | — | CH$_2$COOEt | — | H |

The invention is further defined by reference to the following preparations and examples, which are intended to be illustrative and not limiting.

All temperatures are in degrees Celsius.

PREPARATION 1

1,3-Dihydro-5-(2-fluorophenyl)-3(R)-(3'-indolyl)methyl-2H-1,4-benzodiazepin-2-one 2-Amino-2'-fluorobenzophenone (12.5 g, 58 mmole) was stirred in 100 ml of dry tetrahydrofuran in an ice bath. D-Tryptophan acid chloride hydrochloride (16 g, 62 mmole), slurried in 50 ml of tetrahydrofuran, was added over 10 minutes, and the mixture stirred 2 hours in the ice bath. The resulting solid was filtered, then added to 200 ml of methanol containing 200 ml of water. The pH was adjusted to 8.5-9.0 with 10% sodium hydroxide, the mixture was stirred for three days, then filtered. The solid was dried in vacuo at 40°.

PREPARATION 2

1,3-Dihydro-5-(2-fluorophenyl)-3-(R)-(3'-indolyl)methyl-2H-1,4-benzodiazepin-2-thione 1,3-Dihydro-5-(2-fluorophenyl)-3-(R)-(3'-indolyl)-methyl-2H-1,4-benzodiazepin-2-one (2.5 g, 6.5 mmole) and 2,4-bis-(4-methoxyphenyl)-2,4-dithioxo-1,3,2,4-dithiaphosphetane (1.6 g, 3.95 mmole) (Lawesson's reagent) were combined in toluene (35 ml) and heated at reflux under nitrogen for 45 minutes. The mixture was cooled and added directly to the top of a nine inch (23 cm) column (55 mm diameter) of silica gel (230-400 mesh) and eluted with methylene chloride (CH$_2$Cl$_2$), followed by a gradient of 1% to 5% (v/v) ether in CH$_2$Cl$_2$. The product fractions were combined and evaporated in vacuo to give the title compound as a white solid.

m.p: 147°-148° C.

Pmr: confirmed structure of the title compound

PREPARATION 3

1,3-Dihydro-5-(2-fluorophenyl)-3-(R)-(3'-indolyl)methyl-2H-1,4-benzodiazepin-2-hydrazone The compound from Preparation 2 (0.49 g, 1.22 mmole) and 95% hydrazine (0.24 g, 7.5 mmole) were combined in methanol (8 ml) and stirred at ambient temperature for 30 minutes. An additional 0.24 g of hydrazine was added, and the mixture was stirred another 60 minutes, then poured into ice water (100 ml). The mixture was extracted with methylene chloride (CH$_2$Cl$_2$) (3×50 ml) and the CH$_2$Cl$_2$ layers washed with water, dried over potassium carbonate, filtered, and evaporated to dryness in vacuo to give the title compound.

EXAMPLE 1

6-(2-Fluorophenyl)-4-(R)-4-(3'-indolyl)methyl-1-methyl-4H-s-triazolo[4,3-a]-1,4-benzodiazepine 1,3-Dihydro-5-(2-fluorophenyl)-3-(R)-(3'-indolyl)-methyl-2H-1,4-benzodiazepin-2-hydrazone (0.5 g, 1.26 mmole) and triethyl orthoacetate (1.15 g, 7.1 mmol) were combined in absolute ethanol (15 ml). Concentrated sulfuric acid (0.16 ml) was added and the mixture stirred at ambient temperature for 30 minutes. The acid was neutralized with saturated sodium bicarbonate solution and the mixture evaporated in vacuo. The residue was treated with water (30 ml) and extracted with methylene chloride (CH$_2$Cl$_2$) (3×30 ml). The CH$_2$Cl$_2$ layers were combined, washed with water, dried over potassium carbonate, filtered, and evaporated to dryness in vacuo. The residue was chromatographed on silica gel (230-400 mesh, nine inch (23 cm) column, 25 mm diameter, 1.5% and 4% (v/v) methanol in CH$_2$Cl$_2$ elution), and the product fractions evaporated to dryness in vacuo. The residue was recrystallized from ether to give the title compound: (m.p.: ca. 80° (foam)).

Analysis Calc'd for C$_{26}$H$_{20}$FN$_5$.0.4Et$_2$O.0.5H$_2$O: C, 72.04; H, 5.48;, N, 15.22; Found: C, 72.05; H, 5.13; N, 15.22.

The compound showed a single spot by tlc (R$_f$=0.32, silica gel plate eluted with 5% (v/v) methanol in CH$_2$Cl$_2$.

The nmr spectrum was consistent with the title structure and verified the presence of ether (ca. 0.5 mole), and water.

The compound was 98.8% pure by hplc.

EXAMPLE 2

6-(2-Fluorophenyl)-4(R)-4-(3'-indolyl)methyl-1-phenyl-4H-s-triazolo[4,3-a]-1,4-benzodiazepine Following the procedure of Example 1, 230 mg (0.58 mmole) of 1,3-dihydro-5-(2-fluorophenyl)-3-(R)-(3'-indolyl)methyl-2H-1,4-benzodiazepin-hydrazone and 346 mg (1.9 mmole) of trimethyl orthobenzoate in 10 ml of ethanol were reacted to give the title compound.

The analytical sample was obtained via silica gel chromatography (chloroform-methanol 97:3 v/v elution) and was fully characterized. tlc, hplc: greater than 96% pure ms (14 ev): 483(M+), 383, 354, 284.

PMR (CDCl$_3$): 4.05 (1H, dxd, J=15.9), 4.20 (1H, dxd, J=15.5), 4.34 (1H, dxd, J=9.5), 6.94 (1H, m), 7.03 (1H, m), 7.10 (1H, m), 7.19 (1H, m), 7.25–7.45 (11H, m), 7.56 (1H, m), 7.68 (2H, m), 8.14 (1H, bs, N-H).

Elemental Analysis: $C_{31}H_{22}FN_5 \cdot 0.55CHCl_3$: Calc'd: N, 12.75; C, 68.99; H, 4.14. Found: N, 12.46; C, 69.21; H, 4.31.

EXAMPLE 3

6-(2-Fluorophenyl)-4(R)-4-(3'-indolyl)methyl-4H-s-triazolo[4,3-a]-1,4-benzodiazepine Following the procedure of Example 1, 230 mg (0.58 mmole) of 1,3-dihydro-5-(2-fluorophenyl)-3-(R)-(3'-indolyl)-methyl-2H-1,4-benzodiazepin-2-hydrazone and 203 mg (1.9 mmole) of trimethyl orthoformate were reacted in 5 ml of ethanol in the presence of concentrated sulfuric acid (2 drops) to give 240 mg of the title compound.

The analytical sample was prepared by silica gel chromatography (chloroform-methanol 95:5 v/v elution) and fully characterized. tlc, hplc: greater than 98% pure ms (14 ev): 407 (M+), 278.

pmr (CDCl$_3$): 4.05 (1H, m), 4.17 (1H, m), 4.35 (1H, m), 6.98 (1H, t, J=9), 7.10 (1H, t, J=7), 7.15–7.7(11H, m), 8.12 (1H, b.s., N-H), 8.64 (1H, s, C-H triazole).

Elemental Analysis: $C_{25}H_{18}FN_5 \cdot 0.5 \, CHCl_3$: Calc'd.: N, 14.99; C, 65.56; H, 3.99; Found: N, 14.96; C, 65.81; H, 4.15.

EXAMPLE 4

6-(2-Fluorophenyl)-4(R)-4-(3'-indolyl)methyl-1-dimethylaminomethyl-4H-s-triazolo[4,3-a]-1,4-benzodiazepine 6-(2-Fluorophenyl)-4(R)-4-(3'-indolyl)methyl-4H-s-triazolo[4,3-a]-1,4-benzodiazepine (250 mg, 0.61 mmole) and dimethyl methylene ammonium chloride[1] (80 mg, 0.8 mmole) were combined in 3 ml of degassed dimethylformamide and heated at 80° C. for 3 hours. The reaction mixture was poured into 50 ml of water, made alkaline with sodium hydroxide, and extracted with chloroform (3×75 ml). The combined organic extracts were washed with water (50 ml) and brine, then dried (MgSO$_4$) and rotoevaporated to yield 300 mg of crude product. The analytical product was obtained via silica gel chromatography (methylene chloride-methanol 95:5 v/v) and was fully characterized.

tlc, hplc: greater than 96% pure.
ms (70 ev): 464 (M+), 421, 292.
pmr (CDCl$_3$): 2.63 (6H, s, N(CH$_3$)$_2$), 3.65 (2H, dxd), 4.05 (1H, dxd), 4.13 (1H, dxd), 4.28 (1H, dxd), 6.96 (1H, t), 7.07 (1H, t), 7.15–7.6 (9H, m), 7.68 (1H, d), 8.23 (1H, d), 8.27 (1H, b.s.).

Elemental Analysis: $C_{28}H_{25}FN_6 \cdot 0.22 \, CHCl_3$: Calc'd: N, 17.12; C, 69.05; H, 5.18. Found: N, 17.18; C, 69.00; H, 5.34.

1. Prepared according to procedure in S. Kinast & L. Tietze, *Angew. Chem. Int. Ed.*, (1976) 15, 239; H. Böhme and K. Hartke, *Chem. Ber.*, (1960) 93, 1305.

EXAMPLE 5

2,4-Dihydro-3(R)-(3'-indolyl)methyl-6-(2-fluoro phenyl)-1H-S-triazolo-[4,3-a]-1,4-benzodiazepin-1-one solvate 1,3-Dihydro-3(R)-(3'-indolyl)methyl-6-(2-fluorophenyl)-2H-1,4-benzodiazepin-2-hydrazone (160 mg, 0.40 mmole) and carbonyl diimidazole (324 mg, 2 mmole) were combined in 30 ml of dry tetrahydrofuran at room temperature. The reaction mixture was protected from moisture and allowed to stand overnight. After 14 hours at room temperature the reaction was heated to reflux for 3 hours, cooled and diluted with 150 ml of ethyl acetate. This solution was washed with water (2×50 ml) and brine. The dried organic extracts (MgSO$_4$) were concentrated to yield 300 mg of crude product. Preparative thick layer chromatography (chloroform-methanol-ammonia elution, 95:5:0.5 v/v) afforded the analytical sample.

HPLC: greater than 99% pure.
PMR (CDCl$_3$): according to theory.
MS (70 ev.): 423 (M+), 294.

Elemental Analysis: $C_{25}H_{18}FN_5O \cdot 0.5 \, CHCL_3$; Calc'd: N 14.49; C 63.34; H 3.86; Found: N 14.55; C 63.65; H 4.00.

EXAMPLE 6

1-Trichloromethyl-4(R)-(3'-indolyl)methyl-6-(2-fluorophenyl)-4H-S-triazolo[4,3-a]-1,4-benzodiazepine solvate To a solution of 1 ml of ethanol containing 1,3-dihydro-3(R)-(3'-indolyl)methyl-5-(2-fluorophenyl)-2H-1,4-benzodiazepine-2-hydrazone (90 mg. 0.23 mmole) and trichloroacetonitrile (79 ul, 0.79 mmole) was added 1 drop of concentrated sulfuric acid at room temperature. After four hours, 1 ml of saturated sodium bicarbonate solution was added to the reaction mixture and the solvent was removed under reduced pressure. The residue was dissolved in methylene chloride (20 ml) and washed with water (3×30 ml) and brine. The dried (MgSO$_4$) organic phase was concentrated to give 100 mg of crude product which was chromatographed on silica gel (hexane-ethylacetate, 3:2 v/v) to afford the analytical sample (90 mg).

HPLC: greater than 99% pure.
PMR (CDCl$_3$): according to theory.
MS (70 ev.): 525 (M+) 523, 406, 393.

Elemental Analysis: $C_{26}H_{17}Cl_3FN_5 \cdot 0.5 \, CHCL_3$: Calc'd: N 11.98; C 54.45; H 3.01; Found: N 10.76; C 54.39; H 3.03.

PREPARATION 4

1,3-Dihydro-5-(2-fluorophenyl)-3-benzyloxycarbonylamino-2H-1,4-benzodiazepin-2-thione 1,3-Dihydro-5-(2-fluorophenyl)-3-benzyloxycarbonylamino-2H-1,4-benzodiazepin-2-one (6.5 g, 16.1 mmole) and 2,4-bis-(4-methoxyphenyl)-2,4-dithioxo-1,3,2,4-dithiaphosphetane (4.9 g, 12.1 mmol) were combined in 500 ml of toluene and heated at reflux for 1.5 hours. The reaction mixture was cooled, diluted to 700 ml with ethyl acetate and washed with 10% sodium hydroxide solution (4×50 ml) and brine. The organic phase was dried ($Na_2SO_4$) and concentrated under reduced pressure to yield 12 g of crude product. Trituration with ethyl acetate gave 4.0 g of the analytical product as a yellow powder. Chromatography of the mother liquors on silica gel (hexane-ethyl acetate elution 1:1 v/v) afforded an additional 2.2 g of pure product: m.p. 190°–191° C.

Pmr ($CDCl_3$): confirmed structure of the title compound.

MS (14 ev): 419 (M+), 311, 284, 256, 243, 224.

Elemental Analysis: $C_{23}H_{18}FN_3O_2S$ Calc'd: N, 10.02; C, 65.86; H, 4.33. Found: N, 9.79; C, 65.59; H, 4.44.

PREPARATION 5

1,3-Dihydro-5-(2-fluorophenyl)-3-amino-2H-1,4-benzodiazepin-2-thione

To an equal volume mixture of methylene chloride and acetic acid (400 ml) was added 3.1 g (7.39 mmole) of 1,3-dihydro-5-(2-fluorophenyl)-3-benzyloxy carbonylamino-2H-1,4-benzodiazepin-2-thione. Hydrogen bromide gas was passed into the stirred solution for 6–8 hours. The solvent and excess reagent were removed under reduced pressure to give 8 g of the crude HBr salt as a powder. This material was suspended in methylene chloride, rendered basic with sodium hydroxide solution, and rotoevaporated to dryness. The residue was flash chromatographed on silica gel ($CHCl_3$—$CH_3OH$, 99:1 then $CHCl_3$—$CH_3OH$—$NH_3$, 90:10:1) and afforded 2.4 g of the pure amine.

Pmr ($CDCl_3$/DMSO-$d_6$): confirmed structure of the title compound.

PREPARATION 6

1,3-Dihydro-5-(2-fluorophenyl)-3-(4-chlorophenyl) carbonylamino-2H-1,4-benzodiazepin-2-thione A mixture of 1,3-dihydro-5-(2-fluorophenyl)-3-amino-2H-1,4-benzodiazepin-2-thione (200 mg, 0.70 mmole), 4-chlorobenzoic acid (120 mg, 0.77 mmole), and 1-ethyl-3-(3-dimethylaminopropyl)carbodiimide hydrochloride (150 mg, 0.77 mmole) were combined in 2 ml of dry N,N-dimethylformamide at room temperature. The pH of the homogeneous reaction mixture was then adjusted to 8 with triethylamine. The reaction mixture was protected from moisture and stirred at room temperature overnight (90% complete after 1 hour). The solvent was removed under reduced pressure and the residue dissolved in 100 ml of ethylacetate. The organic phase was then washed in succession with 10% citric acid solution (2×20 ml), saturated sodium bicarbonate solution (20 ml), and brine. The dried ($MgSO_4$) organic phase was rotoevaporated to dryness to yield 300 mg of crude product. Preparative thick layer chromatography on $SiO_2$ (hexane-ethyl acetate, 2:1) gave the analytical sample as a solvate: m.p. 156°–158° C.

Pmr (DMSO-$d_6$): confirmed structure of the title compound.

MS (14 ev): 423 (M+), 391, 284, 268, 236, 139.

Elemental Analysis: $C_{22}H_{15}ClFN_3OS$ 0.10 $C_4H_8O_2$: Calc'd: N, 9.71; C, 62.17; H, 3.68. Found: N, 9.39; C, 62.45; H, 4.01.

PREPARATION 7

1,3-Dihydro-5-(2-fluorophenyl)-3-(2-indole)carbonylamino-2H-1,4-benzodiazepin-2-thione A mixture of 1,3-dihydro-5-(2-fluorophenyl)-3-amino-2H-1,4-benzodiazepin-2-thione (400 mg, 1.40 mmole), indole-2-carboxylic acid (248 mg, 1.54 mmole), and 1-ethyl-3-(3-dimethylaminopropyl) carbodiimide hydrochloride (295 mg, 1.54 mmole) were combined in 10 ml of dry N,N-dimethylformamide at room temperature. The pH of the homogeneous reaction mixture was then adjusted to 8 with triethylamine. The reaction mixture was protected from moisture and stirred at room temperature overnight (50% complete after 1 hour). The solvent was removed under reduced pressure and the residue dissolved in 200 ml of ethylacetate. The organic phase was then washed in succession with 10% citric acid solution (2×25 ml), saturated sodium bicarbonate solution (25 ml), and brine. The dried ($MgSO_4$) organic phase was rotoevaporated to dryness to yield 1.4 g of crude product. Preparative thick layer chromatography on $SiO_2$ (hexane-ethyl acetate, 1:1) gave the analytical sample as a beige powder: m.p. 209°–211° C. Pmr ($CDCl_3$): confirmed structure of the title compound.

MS (14 ev): 428 (M+), 396, 394, 296, 293, 252, 249.

Elemental Analysis: $C_{24}H_{17}FN_4OS$ 0.15 $C_4H_8O_2$. Calc'd: N, 12.69; C, 66.89; H, 4.15. Found: N; 12.92; C, 66.69; H, 3.90.

PREPARATION 8

1,3-Dihydro-5-(2-fluorophenyl)-3-benzyloxycarbonylamino-2H-1,4-benzodiazepin-2-hydrazone Using reaction conditions identical to those described in Preparation 3, 1,3-dihydro-5-(2-fluorophenyl)-3-benzyloxycarbonylamino-2H-1,4-benzodiazepin-2-thione (1.64 g, 3.91 mmole) was converted to the title compound with 2.5 ml of hydrazine (95%) in 35 ml of methanol.

PREPARATION 9

1,3-Dihydro-5-(2-fluorophenyl)-3-(4-chlorophenyl) carbonylamino-2H-1,4-benzodiazepin-2-hydrazone Using reaction conditions identical to those described in Preparation 3, 1,3-dihydro-5-(2-fluorophenyl)-3-(4-chlorophenyl)carbonylamino-2H-1,4-benzodiazepin-2-thione (230 mg, 0.54 mmole) was converted to the title compound with 1 ml of hydrazine (95%) in 5 ml of methanol.

PREPARATION 10

1,3-Dihydro-5-(2-fluorophenyl)-3-(2-indole)carbonylamino-2H-1,4-benzodiazepin-2-hydrazone Using reaction conditions identical to those described in Preparation 3, 1,3-dihydro-5-(2-fluorophenyl)-3-(2-indole)-carbonylamino-2H-1,4-benzodiazepi n-2-thione (1.0 g, 2.33 mmole) was converted to the title compound with 2 ml of hydrazine (95%) in 20 ml of methanol.

EXAMPLE 7

6-(2-Fluorophenyl)-4-(4-chlorophenyl)carbonylamino-4H-s-triazolo[4,3-a]-1,4-benzodiazepine Following the procedure of Example 1, 230 mg (0.54 mmole) of 1,3-dihydro-5-(2-fluorophenyl-3-(4-chlorophenyl)carbonylamino-2H-1,4-benzodiazepin-2-hydrazone and 230 mg (2.17 mmole) of trimethyl orthoformate in 5 ml of ethanol were reacted to give the title compound. The analytical sample was obtained by silica gel chromatography (chloroform-methanol, 97:3) and recrystallization from ethyl acetate ether as white needles: m.p. 250°-251° C.

Pmr (DMSO-$d_6$): 6.38 (1H, d, J=8 Hz, C$_4$proton), 9.36 (1H, s, triazolo proton); spectrum confirms structure. MS (14 ev): 431 (M+), 292.

Elemental Analysis: $C_{23}H_{15}ClFN_5O$: Calc'd: N, 16.22; C, 63.97; H, 3.50. Found: N, 15.92; C, 64.14; H, 3.70.

EXAMPLE 8

6-(2-Fluorophenyl)-4-(indol-2-yl)carbonylamino-4H-s-triazolo[4,3-a]-1,4-benzodiazepine Following the procedure of Example 1, 200 mg (0.46 mmole) of 1,3-dihydro-5-(2-fluorophenyl)-3-(indol-2-yl)carbonylamino-2H-1,4-benzodiazepin-2-hydrazone and 260 mg (2.45 mmole) of trimethyl orthoformate in 5 ml of methanol were reacted to give the title compound. Preparative thick layer chromatogrpahy (chloroform-ethanol-ammonia 90:10:1) followed by recrystallization from ethyl acetate afforded the analytical sample: m.p. 291° C. Pmr (DMSO-$d_6$): 6.44 (1H, d, J=8 Hz, C$_4$proton), 9.37 (1H, s, triazolo proton), 10.15 (1H, d, J=8 Hz, amide NH); spectrum confirms structure assignment. MS (14 ev): 436 (M+), 292, 160.

Elemental Analysis: $C_{25}H_{17}FN_6O·0.10$ $C_4H_8O_2$: Calc'd: N, 18.87; C, 68.51; H, 4.03. Found: N, 18.86; C, 68.45; H, 3.87.

EXAMPLE 9

6-(2-Fluorophenyl)-4-(indol-2-yl)carbonylamino-1-methyl-4H-s-triazolo[4,3-a]-1,4-benzodiazepine Following the procedure of Example 1, 100 mg (0.23 mmole) of 1,3-dihydro-5-(2-fluorophenyl)-3-(indol-2-yl)carbonylamino-2H-1,4-benzodiazepin-2-hydrazone and 260 mg (1.6 mmole) of triethyl orthoacetate in 5 ml of ethanol were reacted to give the title compound. Preparative thick layer chromatography (chloroform-ethanol-ammonia, 90:10:1 and then rechromatography with chloroform-methanol-ammonia 95:5:0.5) afforded the analytical sample: m.p. 294° C. (d).

Pmr (DMSO-$d_6$): 2.6 (3H, s, CH$_3$), 6.32 (1H, d, J=8 Hz, C$_4$proton), 10.10 (1H, d, J=8 Hz, amide NH), 11.10 (1H, br.s., indole NH); spectrum confirms structure and solvate.

MS (14 ev): 450 (M+), 306.

Elemental Analysis: $C_{26}H_{19}FN_6O·0.20$ $C_4H_8O_2$: Calc'd: N, 17.96; C, 68.76; H, 4.44. Found: N, 17.86; C, 68.78; H, 4.52.

EXAMPLE 10

6-(2-Fluorophenyl)-4-benzyloxycarbonylamino-4H-s-triazolo[4,3-a]-1,4-benzodiazepine Following the procedure of Example 1, 1.39 g (3.33 mmole) of 1,3-dihydro-5-(2-fluorophenyl)-3-benzyloxycarbonylamino-2H-1,4-benzodiazepin-2-hydrazone and 5 ml (45.7 mmole) of trimethylorthoformate in 30 ml of methanol were reacted to give the title compound. Silica gel chromatography (chloroform-methanol-ammonia 95:5:0.5 elution) followed by recrystallization from ethyl acetate-ether gave the analytical material as white rosettes: m.p. 123° C.

Pmr (CDCl$_3$): 5.03 (2H, s, benzyl protons), 6.09 (1H, d, J=9 Hz, C$_4$proton), 8.67 (1H, s, triazolo proton); spectrum confirms structure assignment.

MS (14 ev): 427 (M+), 319, 292, 287, 264, 108.

Elemental Analysis: $C_{24}H_{18}FN_5O_2$: Calc'd: N, 16.38; C, 67.43; H, 4.24. Found: N, 16.38; C, 67.26; H, 4.32.

PREPARATION 11

[5-(2-Phenyl)-2,3-dihydro-2-thioxo-1H-1,4-benzodiazepin-3-yl]carbamic acid phenyl methyl ester.

[5-(2-Phenyl)-2,3-dihydro-2-oxo-1H-1,4-benzodiazepin-3-yl]carbamic acid phenyl methyl ester (16 mmole) and Lawesson's reagent (12 mmole) were combined in 500 ml of toluene and heated to reflux for 1.5 hours. The reaction mixture was diluted to 700 ml with ethyl acetate and washed with sodium hydroxide solution (20%, 4×50 mL) and brine (50 mL). The dried organic phase (sodium sulfate) was concentrated in vacuo to yield the crude product as a solid. This material was flash chromatographed on silica gel (hexane-ethyl acetate 1:1 elution) to give the title compound in pure form.

PREPARATION 12

[5-(2-Phenyl)-3-benzyloxycarbonylamino-3H-1,4-benzodiazepin-2-yl]hydrazine.

A solution of 10 mL of methanol containing 350 mg of [5-(2-phenyl)-2,3-dihydro-2-thioxo-1H-1,4-benzodiazepin-3-yl]carbamic acid phenyl methyl ester (0.87 mmole) was treated with 1.5 ml of 95% hydrazine at room temperature. The resulting solution was protected from moisture and stirred for 1.5 hours. The reaction mixture was concentrated and the residual oil was dissolved in ethyl acetate and washed with 50% brine solution and then with saturated brine solution. The organic phase was dried and concentrated to yield 400 mg of the title compound.

PREPARATION 13

6-Phenyl-4-benzyloxycarbonylamino-4H-[1,2,4]triazolo-[4,3-a][1,4]benzodiazepine.

Trimethyl orthoformate (398 mg) and [5-(2-phenyl)-3-benzyloxycarbonylamino-3H-1,4-benzodiazepin-2-yl]hydrazine (300 mg) were combined in 10 mL of methanol. This solution was treated with a catalytic amount of concentrated sulfuric acid at room temperature and was stirred for 60 hours. The reaction mixture was treated with saturated sodium bicarbonate solution (1 mL) and concentrated. The residue was dissolved in methylene chloride and washed with water and brine. Concentration under reduced pressure gave 270 mg of product which was purified by preparative thick layer chromatography on silica gel (95:5:0.5 chloroform-methanol-ammonium hydroxide elution).

PREPARATION 14

6-Phenyl-4H-[1,2,4]triazolo-[4,3-a][1,4]benzodiazepin-4-ylamine formate salt.

To a 4.5% solution of 90% aqueous formic acid in methanol was added 120 mg of 10% palladium on carbon catalyst under nitrogen. To this suspension was added 150 mg of 6-phenyl-4-benzyloxycarbonylamino-4H-[1,2,4]triazolo-[4,3-a][1,4]benzodiazepin. The reaction mixture was stirred under nitrogen at 23° C. for 1.5 hours and filtered through Celite. The filtrate was concentrated under reduced pressure and azeotropically dried with toluene to yield the title compound.

EXAMPLE 11

N-(4-Chlorophenyl)-N'-(6-phenyl-4H-[1,2,4]triazolo-[4,3-a][1,4]benzodiazepin-4-yl)urea 6-Phenyl-4H-[1,2,4]triazolo-[4,3-a][1,4]benzodiazepin-4-ylamine formate salt (200 mg, 0.38 mmole) was combined with 4-chlorophenylisocyanate (57 mg, 0.37 mmole) and triethylamine (57 µL) in 10 mL of dry tetrahydrofuran. The mixture was allowed to stand at room temperature overnight. The analytically pure product, which crystallized from solution was collected and dried: m.p. 294°–296° C.

HPLC=99.9% pure at 214 nm.

NMR (DMSO-D$_6$): Consistent with structure assignment and confirms presence of solvent.

FAB MS: 429 (M+ +1).

Analysis for $C_{23}H_{17}N_6OCl$: Calculated: C, 64.41; H, 4.00; N, 19.60. Found: C, 64.19; H, 4.22; N, 19.27.

PREPARATION 15

1-Methyl-6-phenyl-4-benzyloxycarbonylamino-4H-[1,2,4]triazolo-[4,3-a][1,4]benzodiazepine Employing the procedure of Preparation 13, [5-(2-phenyl)-3-benzyloxycarbonylamino-3H-1,4-benzodiazepin-2-yl]hydrazine (400 mg) and trimethyl orthoacetate (481 mg) were combined to yield 390 mg of crude product which was purified by preparative thick layer chromatography on silica gel (95:5:0.5 chloroform-methanol-ammonium hydroxide elution) to afford 300 mg of the analytical sample.

PREPARATION 16

1-Methyl-6-phenyl-4H-[1,2,4]triazolo-[4,3-a][1,4]benzodiazepin-4-ylamine formate salt.

The title compound was obtained in greater than 95% yield from 1-methyl-6-phenyl-4-benzyloxycarbonylamino-4H-[1,2,4]triazolo-[4,3-a][1,4]benzodiazepine according to the procedure of Preparation 14.

EXAMPLE 12

N-(4-Chlorophenyl)-N'-(1-methyl-6-phenyl-4H-[1,2,4]triazolo[4,3-a][1,4]benzodiazepin-4-yl)urea.

1-Methyl-6-phenyl-4H-[1,2,4]triazolo-[4,3-a][1,4]benzodiazepin-4-ylamine formate salt (180 mg, 0.54 mmole) was combined with 4-chlorophenylisocyanate (83 mg, 0.54 mmole) and triethylamine (84 µL) in 5 mL of dry tetrahydrofuran. The mixture was allowed to stand at room temperature overnight. The analytically pure product was obtained by preparative thick layer chromatography on silica gel (94:6:0.6, chloroform-methanol-ammonium hydroxide elution): m.p. 292°–294° C.

HPLC=98.2% pure at 214 nm.

NMR (DMSO-D$_6$): Consistent with structure assignment and confirms presence of solvent.

FAB MS: 443 (M+ +1).

Analysis for $C_{24}H_{19}N_6OCl \cdot 0.35 H_2O$: Calculated: C, 64.16; H, 4.42; N, 18.71. Found: C, 64.33; H, 4.73; N, 18.50.

What is claimed is:

1. A method of treating panic disorder or anxiety disorder in a mammal which comprises administering to said mammal a therapeutically effective amount of a compound of the formula:

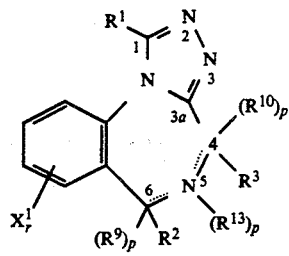

wherein
$R^1$ is H, OH, loweralkyl, cycloloweralkyl, loweralkenyl, substituted or unsubstituted phenyl(wherein the substituents are 1 or 2 of halo, loweralkyl, loweralkoxy, or hydroxy), —(CH$_2$)$_m$NR$^4$R$^5$, CX$^{10}$$_3$, or —(CH$_2$)$_n$COOR$^6$;

$R^2$ is H, loweralkyl, substituted or unsubstituted phenyl (wherein the substitutents are 1 or 2 of halo, loweralkyl, loweralkoxy, loweralkylthio, carboxyl, carboxyloweralkyl, nitro, —CF$_3$,

or hydroxy), or —(CH$_2$)$_m$COOR$^6$;

$R^3$ is

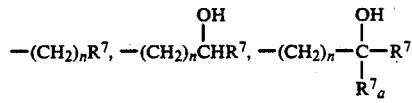

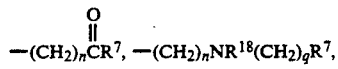

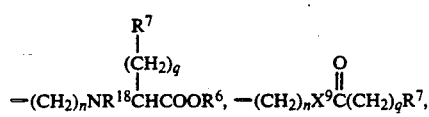

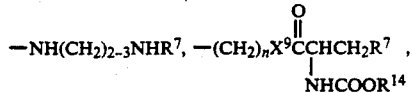

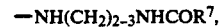

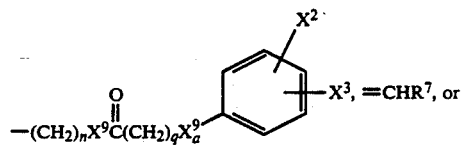

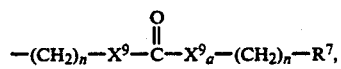

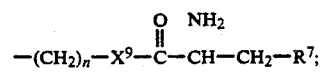

$R^4$ and $R^5$ are independently H, loweralkyl, or cycloloweralkyl or are connected to form a hetero ring

wherein n is 2-6;

R[6] is H, loweralkyl, cycloloweralkyl, substituted or unsubstituted phenyl (wherein the substituents are 1 or 2 of halo, loweralkyl, loweralkoxy, nitro, or CF$_3$), or substituted or unsubstituted phenylloweralkyl (wherein the substituents may be 1 or 2 of halo, loweralkyl, loweralkoxy, nitro, or CF$_3$);

R[7] and R[7]$_a$ are independently α- or β-naphtyl, substituted or unsubstituted phenyl (wherein the substituents are 1 to 2 of halo, —NO$_2$, —OH, —NR[4]R[5], lower alkyl, cyano, phenyl, trifluoromethyl, acetylamino, acetyloxy, loweralkylthio, SCF$_3$, —C≡CH, CH$_2$SCF$_3$, OCHF$_2$, SH, S-phenyl, PO$_3$H, or loweralkoxy),

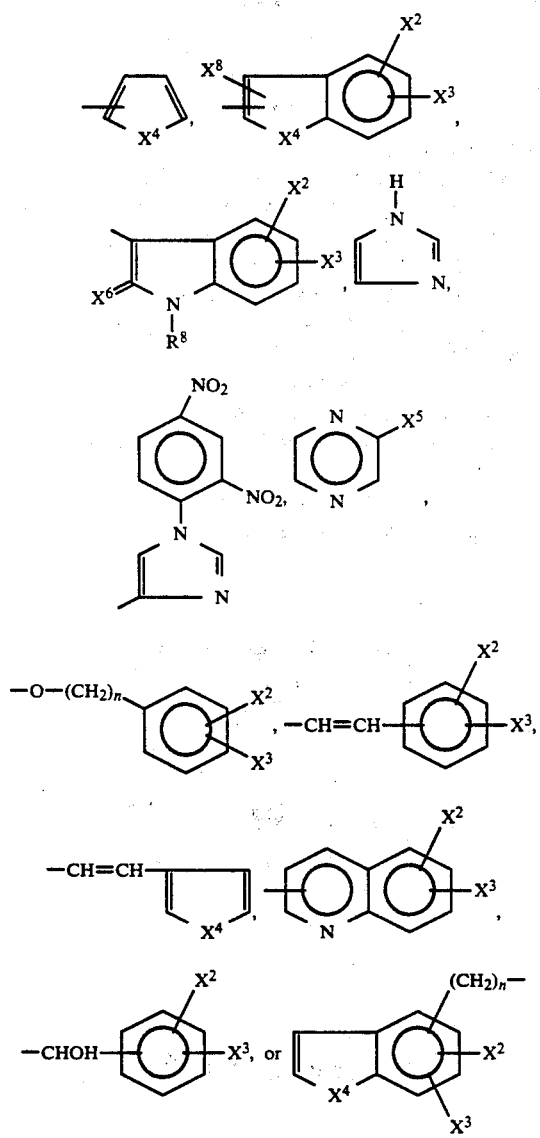

(with the proviso that q is not 0 or 1 in —(CH$_2$)$_n$NH(CH$_2$)$_q$R[7] and that q is not 0 in

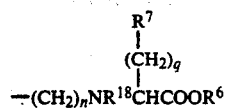

when R[7] or R[7]$_a$ is

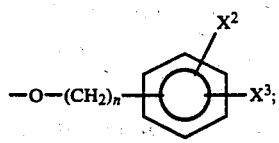

R[8] is H, loweralkyl, cycloloweralkyl, —(CH$_2$)$_m$CONH$_2$, —(CH$_2$)$_m$COOR[6], —(CH$_2$)$_n$-cycloloweralkyl, —(CH$_2$)$_m$NR4R5,

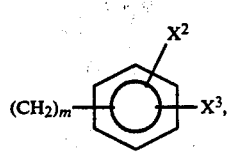

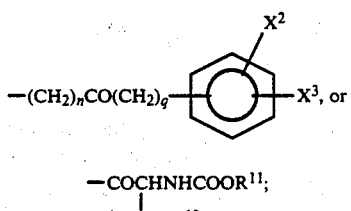

R[9] and R[10] are independently H, —OH, or —CH$_3$;
R[11] and R[12] are independently loweralkyl or cycloloweralkyl;
R[13] is H, loweralkyl, acyl, O, or cycloloweralkyl;
R[14] is loweralkyl or phenylloweralkyl;
R[18] is H, loweralkyl, or acyl;
m is 1-4;
n is 0-4;
p is 0 when its adjacent    is unsaturated or when R[3] is =CHR[7], and it is 1 when its adjacent    is saturated, except that when R[13] is O, p=1 and    is unsaturated;
q is 0-4;
r is 1 or 2;
X[1] is H, —NO$_2$, CF$_3$ CN, OH, loweralkyl, halo, loweralkylthio, loweralkoxy, —(CH$_2$)$_n$COOR[6], —NR[4]R[5],

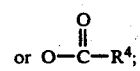

X[2] and X[3] are independently H, —OH, —NO$_2$, halo, loweralkylthio, loweralkyl, loweralkoxy or

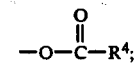

X[4] is S, O, CH$_2$, or NR[8];
X[5] is H, CF$_3$, CN, —COOR[6], NO$_2$, or halo;
X[6] is O or HH;
X[8] is H or loweralkyl;

$X^9$ and $X^9_a$ are independently $NR^{18}$, O;

$X^{10}$ is F, Cl, Br;

╌╌╌ is a saturated or unsaturated bond, such that both bonds in the 7-membered ring of Formula I may be saturated (single bonds but both may not be unsaturated double bonds);

or a pharmaceutically acceptable salt thereof, and a pharmaceutically acceptable carrier.

2. A method of treating oncology disorders, controlling pupil constriction in the eye, or treating withdrawal response produced by chronic treatment or abuse of drugs or alcohol in a mammal which comprises administering to said mammal a therapeutically effective amount of a compound of the formula:

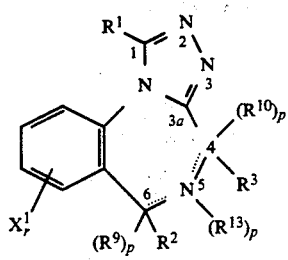

wherein $R^1$ is H, OH, loweralkyl, cycloloweralkyl, loweralkenyl, substituted or unsubstituted phenyl (wherein the substituents are 1 or 2 of halo, loweralkyl, loweralkoxy, or hydroxy), $-(CH_2)_m NR^4 R^5$, $CX^{10}_3$, or $-(CH_2)_n COOR^6$;

$R^2$ is H, loweralkyl, substituted or unsubstituted phenyl (wherein the substitutents are 1 or 2 of halo, loweralkyl, loweralkoxy, loweralkylthio, carboxyl, carboxyloweralkyl, nitro, $$-CF_3, \overset{O}{\underset{\|}{O}}C-R^4$$

or hydroxy), or $-(CH_2)_m COOR^6$;

$R^3$ is

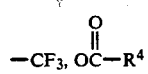

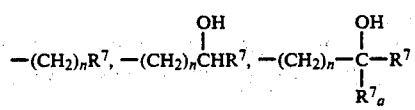

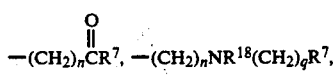

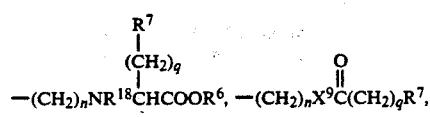

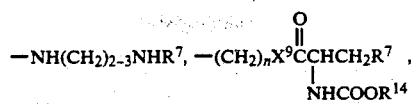

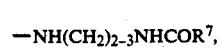

-continued

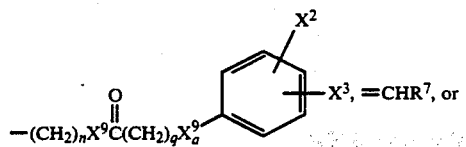

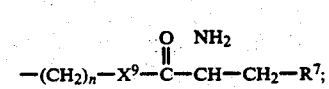

$R^4$ and $R^5$ are independently H, loweralkyl, or cycloloweralkyl or are connected to form a hetero ring

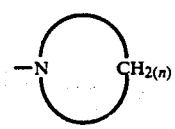

wherein n is 2–6;

$R^6$ is H, loweralkyl, cycloloweralkyl, substituted or unsubstituted phenyl (wherein the substituents are 1 or 2 of halo, loweralkyl, loweralkoxy, nitro, or $CF_3$), or substituted or unsubstituted phenylloweralkyl (wherein the substituents may be 1 or 2 of halo, loweralkyl, loweralkoxy, nitro, or $CF_3$);

$R^7$ and $R^7_a$ are independently α- or β-naphthyl, substituted or unsubstituted phenyl (wherein the substituents are 1 to 2 of halo, $-NO_2$, $-OH$, $-NR^4R^5$, lower alkyl, cyano, phenyl, trifluoromethyl, acetylamino, acetyloxy, loweralkylthio, $SCF_3$, $-C\equiv CH$, $CH_2SCF_3$, $OCHF_2$, SH, S-phenyl, $PO_3H$, or loweralkoxy),

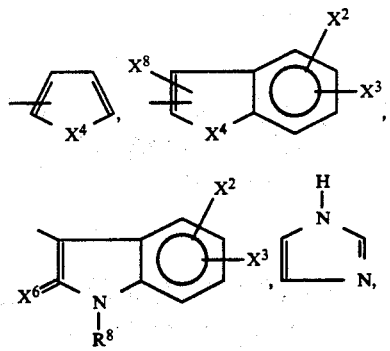

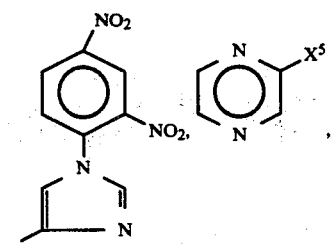

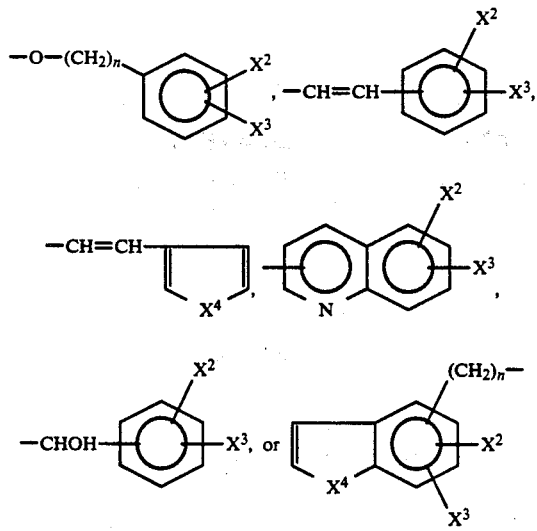

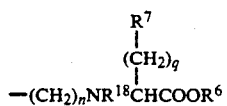

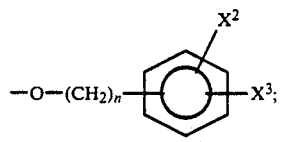

(with the proviso that q is not 0 or 1 in —(CH₂)ₙNH(CH₂)qR⁷ and that q is not 0 in $$-(CH_2)_n NR^{18} \overset{\underset{(CH_2)_q}{|}}{\underset{|}{C}} HCOOR^6$$

when R⁷ or R⁷ₐ is

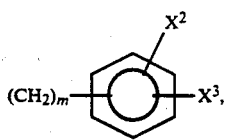

R⁸ is H, loweralkyl, cycloloweralkyl, —(CH₂)ₘCONH₂, —(CH₂)ₘCOOR⁶, —(CH₂)ₙ-cycloloweralkyl, —(CH2)ₘNR4R5,

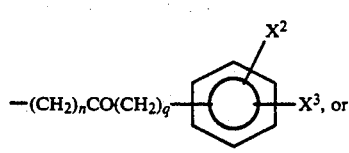

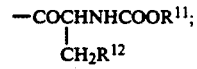

R⁹ and R¹⁰ are independently H, —OH, or —CH₃;
R¹¹ and R¹² are independently loweralkyl or cycloloweralkyl;
R¹³ is H, loweralkyl, acyl, O, or cycloloweralkyl;
R¹⁴ is loweralkyl or phenylloweralkyl;
R¹⁸ is H, loweralkyl, or acyl;
m is 1–4;
n is 0–4;
p is 0 when its adjacent --- is unsaturated or when R³ is =CHR⁷, and it is 1 when its adjacent --- is saturated, except that when R¹³ is O, p=1 and --- is unsaturated;
q is 0–4;
r is 1 or 2;
X¹ is H, —NO₂, CF₃ CN, OH, loweralkyl, halo, loweralkylthio, loweralkoxy, —(CH₂)ₙCOOR⁶, $$-NR^4R^5, \text{ or } O-\overset{O}{\underset{\|}{C}}-R^4;$$

X² and X³ are independently H, —OH, —NO₂, halo, loweralkylthio, loweralkyl, loweralkoxy or $$-O-\overset{O}{\underset{\|}{C}}-R^4;$$

X⁴ is S, O, CH₂, or NR⁸;
X⁵ is H, CF₃, CN, —COOR⁶, NO₂, or halo;
X⁶ is O or HH;
X⁸ is H or loweralkyl;
X⁹ and X⁹ₐ are independently NR¹⁸, O;
X¹⁰ is F, Cl, Br;
---- is a saturated or unsaturated bond, such that both ---- bonds in the 7-membered ring of Formula I may be saturated (single bonds but both may not be unsaturated double bonds);
or a pharmaceutically acceptable salt thereof, and a pharmaceutically acceptable carrier.

3. The method according to claim 1, wherein the therapeutically effective amount of the compound of Formula I is from about 0.005 mg/kg to about 50 mg/kg of body weight, administered to said mammal in a single or divided dose.

4. The method according to claim 2, wherein the therapeutically effective amount of the compound of Formula I is from about 0.005 mg/kg to about 50 mg/kg of body weight, administered to said mammal in a single or divided dose.

5. The method according to claim 1, wherein said mammal is a human.

6. The method according to claim 2, wherein said mammal is a human.